(12) United States Patent
Kharraz Tavakol et al.

(10) Patent No.: US 12,340,348 B2
(45) Date of Patent: *Jun. 24, 2025

(54) METHOD AND APPARATUS FOR MANAGING PHYSICIAN REFERRALS

(71) Applicant: Zocdoc, Inc., New York, NY (US)

(72) Inventors: Oliver D. Kharraz Tavakol, Brooklyn, NY (US); Nikhil Ganju, New York, NY (US); Cyrus E. Massoumi, New York, NY (US)

(73) Assignee: Zocdoc, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/244,742

(22) Filed: Sep. 11, 2023

(65) Prior Publication Data
US 2023/0419258 A1    Dec. 28, 2023

Related U.S. Application Data

(63) Continuation of application No. 17/209,813, filed on Mar. 23, 2021, now Pat. No. 11,790,319, which is a continuation of application No. 15/858,451, filed on Dec. 29, 2017, now Pat. No. 10,997,555, which is a continuation of application No. 12/916,780, filed on Nov. 1, 2010, now abandoned, which is a
(Continued)

(51) Int. Cl.
| | |
|---|---|
| *G16H 40/20* | (2018.01) |
| *G06Q 10/10* | (2023.01) |
| *G06Q 40/08* | (2012.01) |
| *G06Q 50/22* | (2018.01) |
| *G16H 10/60* | (2018.01) |

(52) U.S. Cl.
CPC ............. *G06Q 10/10* (2013.01); *G06Q 40/08* (2013.01); *G06Q 50/22* (2013.01); *G16H 10/60* (2018.01); *G16H 40/20* (2018.01)

(58) Field of Classification Search
None
See application file for complete search history.

(56) References Cited

U.S. PATENT DOCUMENTS 10,997,555 B1 *  5/2021  Kharraz Tavakol ... G06Q 10/10
11,790,319 B2 * 10/2023  Kharraz Tavakol ... G16H 40/20
                                                          705/2
(Continued)

*Primary Examiner* — Robert A Sorey
(74) *Attorney, Agent, or Firm* — White and Williams LLP

(57) ABSTRACT

Method and apparatus for managing the physician referral process, whereby a referring physician (e.g., a primary care provider) refers a patient to another physician (e.g., a specialist) for a particular medical procedure, analysis or care. An aggregator provides systems and methods available to physicians and their administrative staff (herein collectively referred to as physicians or doctors) to: book appointments on behalf of their patients online through a doctor directory and calendar function; filter available doctors by specialty, subspecialty, procedure, insurance participation and/or hospital network; transfer a patient's personal information, medical history and pre-selected insurance forms from one doctor's office to another's, electronically; transfer and upload relevant forms and paperwork via fax from one doctor's office to another; track referrals historically (over time) on a by-doctor or by-patient basis; facilitate referrals to and from doctors in a certain network or group.

22 Claims, 18 Drawing Sheets

Case 1 - Referral Cockpit to Referral Cockpit

1. Patient visits doctor, doctor performs diagnosis and determines need for referral
2. Doctor uses PC to log in to Referral Cockpit; request information on availability of applicable doctors
3. PC sends request to aggregator server
4. Server searches connected database.
5. Server returns requested information to PC/doctor, doctor then uses PC to choose specialist to refer to, book appointment, and transfer patient's records electronically to aggregator server
6. Server forwards records, reservation to specialist's PC via server/database
7. Specialist uses PC to log in to Referral Cockpit and view appointment; contacts patient to confirm appointment; give preparatory instructions, etc.
8. After appointment, specialist uses PC to log into Referral Cockpit and transfer updated records back to doctor via aggregator server

Related U.S. Application Data continuation-in-part of application No. 12/722,728, filed on Mar. 12, 2010, now Pat. No. 10,185,929, said application No. 12/210,690 is a continuation of application No. 12/210,765, filed on Sep. 15, 2008, now Pat. No. 8,688,466, said application No. 12/210,664 is a continuation-in-part of application No. 12/210,716, filed on Sep. 15, 2008, now abandoned, said application No. 12/722,728 is a continuation-in-part of application No. 12/210,690, filed on Sep. 15, 2008, now abandoned, said application No. 12/210,765 is a continuation-in-part of application No. 12/210,664, filed on Sep. 15, 2008, now abandoned.

(56) References Cited

U.S. PATENT DOCUMENTS

| | | | |
|---|---|---|---|
| 2003/0195838 A1* | 10/2003 | Henley | G06Q 30/0212 705/37 |
| 2004/0122790 A1* | 6/2004 | Walker | A61B 5/318 |
| 2004/0236601 A1* | 11/2004 | Summers | G06Q 10/06311 705/2 |
| 2006/0106644 A1* | 5/2006 | Koo | G16H 10/60 715/224 |
| 2007/0083403 A1* | 4/2007 | Baldwin | G06Q 10/10 705/346 |
| 2007/0162310 A1* | 7/2007 | Schmidt | G16H 20/00 600/300 |
| 2008/0262873 A1* | 10/2008 | Bayne | G16H 10/60 705/2 |
| 2009/0089085 A1* | 4/2009 | Schoenberg | G16H 40/20 705/2 |
| 2010/0017222 A1* | 1/2010 | Yeluri | G16H 40/20 705/2 |
| 2010/0037067 A1* | 2/2010 | Rangadass | G06F 9/46 726/1 |
| 2012/0123790 A1* | 5/2012 | Kenyon | G16H 40/20 705/2 |

* cited by examiner

Booking History — 130

Date Range: 1/15/2009 to 1/31/2009 — 132, 133

Patient: leave blank for all — 134

Physician: leave blank for all — 135

Specialty: All Specialties — 136

Sort By: Patient name (Last, First) — 137

Generate Report — 138

| Appointment Status | Patient name & Phone number | Referred to | Appointment Date | Appointment History | Suggested actions |
|---|---|---|---|---|---|
| Awaiting Confirmation ☒ | Michael Smith 212-499-3737 | Alexander Arkansas Cardiologist Carotid Doppler | May 24, 2010 4:00pm - 5:30pm | Booked on 5/2/2010 | |
| Awaiting Confirmation ☒ | Samuel Smith 212-499-3737 | Linda Franks Dermatologist Botox treatment | May 10, 2010 2:00pm - 3:00pm | Booked on 5/1/2010 | |
| Confirmed ⊙ | Frank Smith 212-499-3737 | Vandana Kumra ENT Doctor Allergy Consultation | May 8, 2010 10:00am - 12:00pm | Booked on 4/28/2010 Confirmed on 5/5/2010 | |
| Rescheduled ⊘ | James Smith 212-499-3737 | Roman Dworecki Opthamologist Contact Lenses | May 5, 2010 11:00am - 12:00pm | Booked on 4/20/2010 Rescheduled on 4/26/2010 | |
| Patient Cancelled ⊘ | Johann Smith 212-499-3737 | Scot Rubenstein Podiatrist Bunion | May 2, 2010 1:00pm - 2:00pm | Booked on 4/18/2010 Cancelled on 4/26/2010 | |
| Received Results ✦ | Richard Smith 212-499-3737 | Juan Cartos Rodriguez Orthopedist Back Problems | May 1, 2010 10:00am - 11:00am | Booked on 4/24/2010 Confirmed on 4/29/2010 | Contact Patient |
| Awaiting Results ☒ | Sarah Smith 212-499-3737 | Adele Cavalli OB/GYN OB/GYN Consultation | April 28, 2010 3:00pm - 4:00pm | Booked on 4/20/2010 Rescheduled on 4/25/2010 | |
| Practice Cancelled ⊙ | Barbara Smith 212-499-3737 | Dorina Druckman Physiatrist Theraputic Exercise | April 25, 2010 2:30pm - 3:30pm | Booked on 4/18/2010 Cancelled on 4/24/2010 | Contact Practice |
| Received Results ✦ | Helena Smith 212-499-3737 | Morris Nejat Allergist Allergic Cough | April 23, 2010 10:45am - 11:30am | Booked on 4/17/2010 | |
| Patient No-Show | Robert Smith 212-499-3737 | Karen Wagner Radiologist X-Ray | April 20, 2010 11:30pm - 12:30pm | Booked on 4/15/2010 | Contact Patient |

FIG. 9

Booking History — 170

Date Range: 1/15/2009 to 1/31/2009
patient: leave blank for all    Physician
Sort By: Patient name (Last, First) ▼

| Appointment Status | Results | Patient name & Phone |
|---|---|---|
| Awaiting Confirmation ⊗ | | Michael Smith 212-499-3737 |
| Awaiting Confirmation ⊗ | | Samuel Smith 212-499-3737 |
| Confirmed ⊘ | | Frank Smith 212-499-3737 |
| Rescheduled ⊘ | | James Smith 212-499-3737 |
| Patient Cancelled ⊘ | | Johann Smith 212-499-3737 |
| Received Results ✱ | 📱 | Richard Smith 212-499-3737 |
| Awaiting Results ⊘ | | Sarah Smith 212-499-3737 |
| Practice Cancelled ⊘ | | Barbara Smith 212-499-3737 |
| Received Results ✱ | 📱 | Helena Smith 212-499-3737 |
| Patient No-Show ⊘ | | Robert Smith 212-499-3737 |

— 171

Patient: Richard Smith    — 172, 173    Close ×

Referral Summary | Referral History

Referred to:  Juan Carlos Rodriguez
Specialty:    Cardiologist
Reason:       Back Problems
Date/Time:    May 1, 2010, 10:00am-11:00am    ✱ Received Results

— 174

Insurance Forms
📎 Anthem Blue Cross Blue Shield - Referral Form — 176
Attachments — 175                                    177
📎 rs-charts-2010-01-20.pdf              download     □ re-fax
📎 referral_notes-2010-01-20.txt         download     ☒ re-fax — 178
📎 rs-quest-CBFB_MYH11......14.pdf       download     ☒ re-fax — 179
add another attachment — 180                         remove
                                                     remove
                                         Re-Fax Selected ⚑ — 181

Results
📎 rs-ekg-2010-01-20.pdf — 182, 183

Send Message to Patient
                              — 184
                                                     Send Message ⚑ — 185

Karen Wagner                                         186
Radiologist          April 20, 2010
X-Ray                11:30pm - 12:30pm               Booked on 4/15/2010

Send Message to Doctor

Suggested actions

Contact Patient

Contact Practice

Contact Patient

FIG. 10

Booking History — 190

Date Range: 1/15/2009 to 1/31/2009
patient: leave blank for all    Physician
Sort By: Patient name (Last, First) ▼

| Appointment Status | Results | Patient name & Phone |
|---|---|---|
| ⊠ Awaiting Confirmation | | Michael Smith 212-499-3737 |
| ⊠ Awaiting Confirmation | | Samuel Smith 212-499-3737 |
| ⊙ Confirmed | | Frank Smith 212-499-3737 |
| ⊙ Rescheduled | | James Smith 212-499-3737 |
| ⊙ Patient Cancelled | | Johann Smith 212-499-3737 |
| ✶ Received Results | 📱 | Richard Smith 212-499-3737 |
| ⊠ Awaiting Results | | Sarah Smith 212-499-3737 |
| ⊙ Practice Cancelled | | Barbara Smith 212-499-3737 |
| ✶ Received Results | 📱 | Helena Smith 212-499-3737 |
| 🚫 Patient No-Show | | Robert Smith 212-499-3737 |

— 191

Patient: Richard Smith — 172    Close ✕

Referral Summary | Referral History

Referred to: Juan Carlos Rodriguez
Specialty: Cardiologist
Reason: Back Problems
Date/Time: May 1, 2010, 10:00am – 11:00am ◆ Received Results — 173

Audit Trail — 194
☐ 05/04/2010: Results rs-ekg-2010-01-20.pdf added — 195
☒ 05/02/2010: Message sent to doctor  hide message — 196

Lorem ipsum dolor sit amet, consectetur adipiscing elit. Nam sit amet justo eros, vitae luctus velit Suspendisse sodales nunc nec lectus mattis iaculis. Donec fermentum eros at eros tristique vel condimentum enim condimentum. praesent sollicitudin, neque vel placerat egestas, risus nisi eleifend ligula, sed accumsan massa arcu ut lorem. Aliquam erat volupat. Mauris ultricies augue vitae ☒ 05/29/2010: Message sent to patient    show message — Contact Patient 197
⊙ 04/28/2010: Patient Confirmed — 198
📎 04/28/2010: Attachment rs-charts-2010-01-20.pdf faxed — 199
📎 04/28/2010: Attachment rs-charts-2010-01-20.pdf added — 200
📎 04/25/2010: Attachment referral_notes-2010-02-03.txt faxed — 201
📎 04/25/2010: Attachment referral_notes-2010-02-03.txt faxed — Contact Practice 202
📎 04/25/2010: Attachment rs-quest-CBFB_MYH11.....14.pdf added — 203
📎 04/24/2010: Referral booked — Contact Patient 204

Karen Wagner            April 20, 2010              Booked on 4/15/2010
Radiologist             11:30pm – 12:30pm
X-Ray Sugested actions

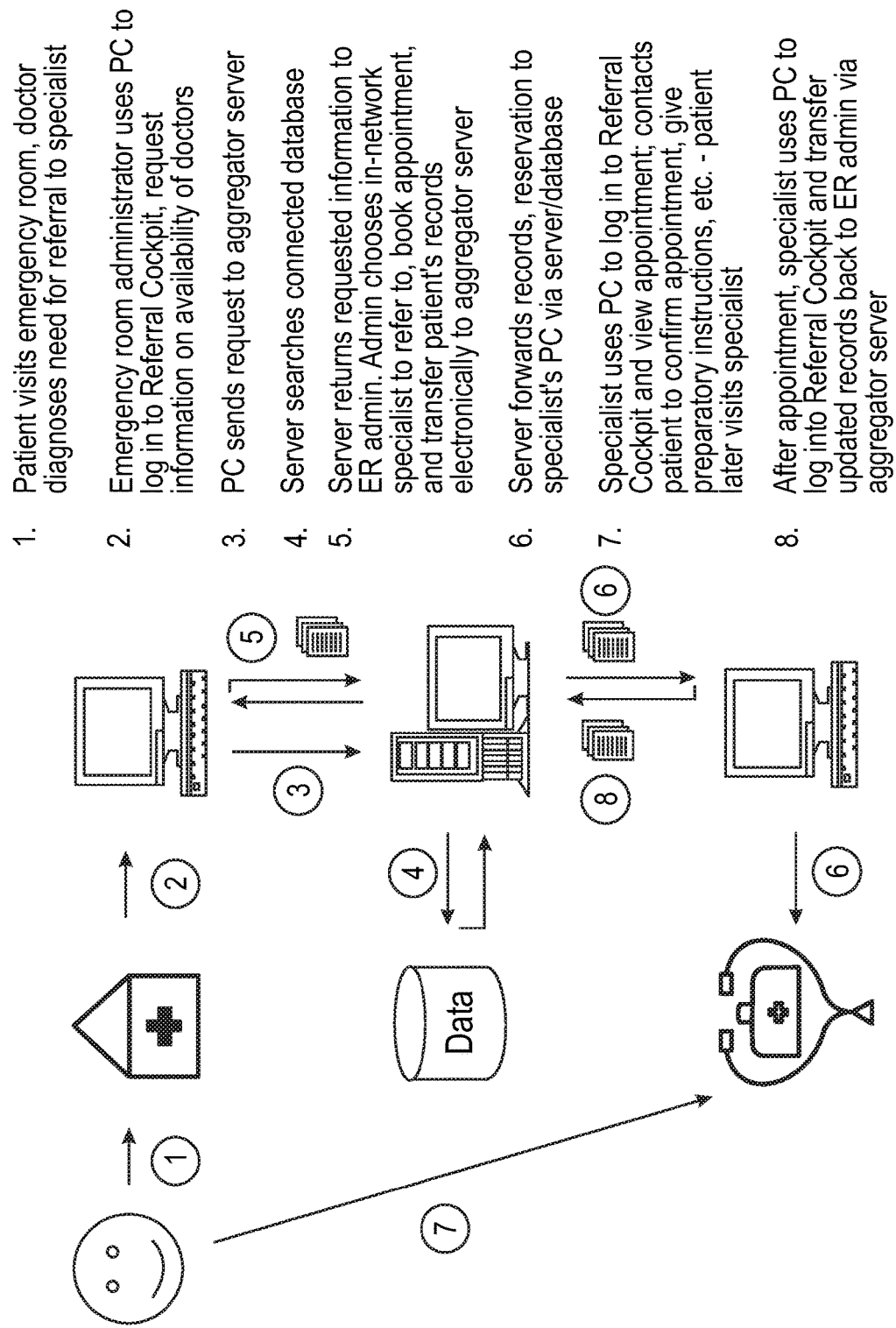
FIG. 15 — Case 5 - Referral within a hospital system

Paper record transfer via aggregator server / database

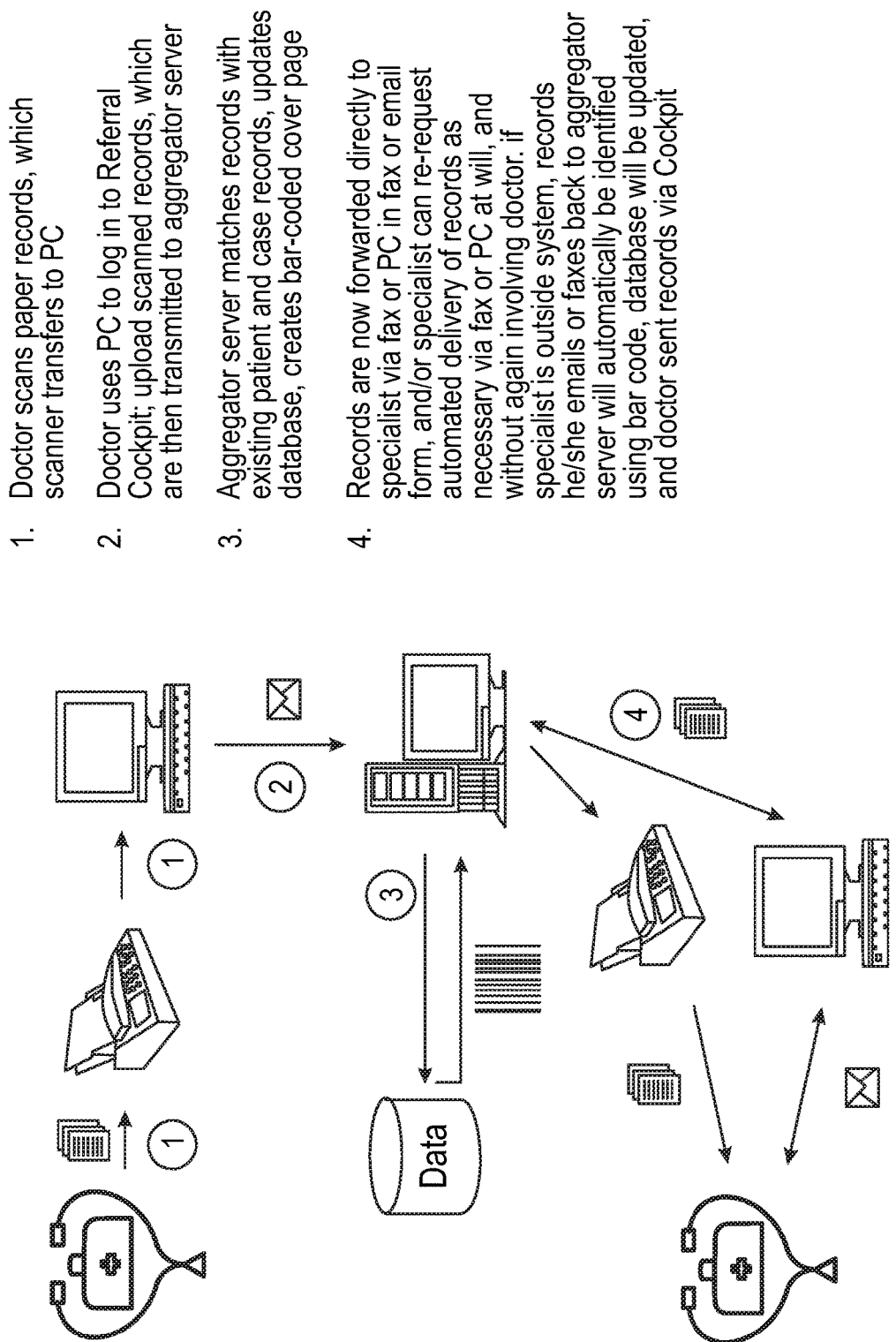

1. Doctor scans paper records, which scanner transfers to PC

2. Doctor uses PC to log in to Referral Cockpit; upload scanned records, which are then transmitted to aggregator server 3. Aggregator server matches records with existing patient and case records, updates database, creates bar-coded cover page 4. Records are now forwarded directly to specialist via fax or PC in fax or email form, and/or specialist can re-request automated delivery of records as necessary via fax or PC at will, and without again involving doctor. if specialist is outside system, records he/she emails or faxes back to aggregator server will automatically be identified using bar code, database will be updated, and doctor sent records via Cockpit

FIG. 16

| ID | PracticeID | DoctorID | LocationID | ProcedureID | StartTime | EndTime | UserID | Duration |
|---|---|---|---|---|---|---|---|---|
| 277 | 1042 | 80 | 25 | 67 | 9/11/2010 8:00 | 9/11/2010 9:00 | 113236 | 60 |
| 281 | 1042 | 80 | 24 | 49 | 9/13/2010 9:00 | 9/13/2010 10:00 | 95754 | 60 |
| 282 | 1042 | 80 | 25 | 23 | 9/13/2010 10:30 | 9/13/2010 11:30 | 159753 | 60 |
| 283 | 1040 | 82 | 23 | 51 | 9/11/2010 10:00 | 9/11/2010 11:00 | 173816 | 60 |
| 284 | 1040 | 82 | 23 | 54 | 9/11/2010 11:00 | 9/11/2010 12:30 | 48151 | 90 |
| 290 | 1038 | 73 | 21 | 72 | 9/18/2010 10:00 | 9/18/2010 11:00 | 173231 | 60 |
| 291 | 1038 | 73 | 21 | 84 | 9/19/2010 13:00 | 9/19/2010 14:30 | 107416 | 90 |
| 293 | 1042 | 80 | 25 | 71 | 9/13/2010 8:00 | 9/13/2010 9:00 | 82743 | 60 |
| 294 | 1042 | 80 | 25 | 69 | 9/13/2010 12:30 | 9/13/2010 13:30 | 169018 | 60 |
| 295 | 1042 | 80 | 25 | 41 | 9/13/2010 15:30 | 9/13/2010 18:30 | 204255 | 180 |
| 296 | 1043 | 83 | 26 | 85 | 9/18/2010 10:00 | 9/18/2010 13:00 | 111058 | 180 |
| 297 | 1043 | 85 | 26 | 26 | 9/18/2010 10:00 | 9/18/2010 18:00 | 47974 | 480 |
| 298 | 1043 | 86 | 27 | 35 | 9/22/2010 14:00 | 9/22/2010 15:00 | 144449 | 60 |
| 299 | 1043 | 83 | 27 | 79 | 9/18/2010 14:00 | 9/18/2010 18:00 | 57600 | 240 |
| 301 | 1043 | 83 | 26 | 74 | 9/12/2010 10:00 | 9/12/2010 18:00 | 148087 | 480 |
| 302 | 1043 | 85 | 26 | 37 | 9/12/2010 10:00 | 9/12/2010 13:00 | 177981 | 180 |
| 304 | 1037 | 71 | 20 | 44 | 9/12/2010 8:15 | 9/12/2010 8:30 | 145726 | 15 |
| 305 | 1037 | 67 | 20 | 25 | 9/12/2010 8:15 | 9/12/2010 9:15 | 115173 | 60 |

FIG. 18

METHOD AND APPARATUS FOR MANAGING PHYSICIAN REFERRALS

This application is a continuation of U.S. patent application Ser. No. 17/209,813, filed Mar. 23, 2021, now U.S. Pat. No. 11,790,319, which is a continuation of U.S. patent application Ser. No. 15/858,451, filed Dec. 29, 2017, now U.S. Pat. No. 10,997,555, which is a continuation of U.S. patent application Ser. No. 12/916,780, filed Nov. 1, 2010, now abandoned, which is a continuation-in-part of U.S. patent application Ser. No. 12/722,728, filed Mar. 12, 2010, now U.S. Pat. No. 10,185,929, which is a continuation of U.S. patent application Ser. No. 12/210,765, filed Sep. 15, 2008, now U.S. Pat. No. 8,688,466, which is a continuation-in-part of Ser. No. 12/210,690 filed Sep. 15, 2008, now abandoned, which is a continuation-in-part of Ser. No. 12/210,664, filed Sep. 15, 2008, now abandoned, which is a continuation-in-part of Ser. No. 12/210,716, filed Sep. 15, 2008, now abandoned, the contents of which applications are hereby incorporated by reference in their entirety.

FIELD OF THE INVENTION

The present invention relates to a method and apparatus for managing the physician referral process, whereby a referring physician (e.g., a primary care provider) refers a patient to another physician (e.g., a specialist) for a particular medical procedure, analysis or care.

BACKGROUND

Comprehensive medical care often requires a patient to visit more than just one doctor. While many patients have an established and long-standing relationship with their primary care provider, they are generally unfamiliar with more specialized doctors until medical circumstances necessitate a referral to one. Upon receiving a referral, the patient is usually the one left to arrange an actual appointment with the specialist. There is little transparency in this process, and under unfavorable circumstances a patient may find himself/ herself referred to a doctor with little to no near-term availability, or a doctor who no longer accepts his or her insurance. These hurdles may cause delays in medical care, and in some cases even dissuade patients from complying with their primary care provider's recommendation to seek additional medical care from a specialist.

One proposed solution is for the primary care provider to use a remote desktop session with the secondary care provider's office to make an appointment while the patient is in communication (e.g., on the phone) with the primary care provider. This is not a desirable solution because:
 a) the primary care provider needs to have remote desktop access to the secondary care provider's office, which is a security risk;
 b) the primary care provider's phone agent needs to be trained on how to use the scheduling software in the secondary care office correctly, and since there are potentially many different offices and scheduling systems, this is not feasible nor scalable;
 c) the primary care agent attempting to schedule the appointment does not know the rules about when appointments can be made with the secondary care provider, so often the appointment is not made.

The problems do not end with booking the referral appointment. There is no protocol for rescheduling missed or canceled appointments, sharing of patient information between the primary and secondary care offices, follow-up appointments with the primary care provider, etc.; each of these additional steps require someone to reestablish communication between one or more of the patient's primary care physician and the secondary care physician. The inefficiencies in managing this process are a drain on both the primary and secondary physicians. The patient, who has the least amount of medical knowledge and often an inability to anticipate or articulate the critical nature or timing of the referral, is left calling one or both offices and communicating with a receptionist who cannot independently determine what the next step in the process should be, without again involving either the primary or secondary care physicians.

The issues described above have been long-standing problems for both physicians and patients, and substantially interfere with the ability to provide appropriate and cost effective medical care.

SUMMARY OF THE INVENTION

In one or more embodiments of the invention, an apparatus and method are provided that allows doctors and their administrative staff to manage the process of physician referrals, whereby a patient is referred from one physician (the referring physician) to another physician (the referred-to or receiving physician) for a particular medical procedure, or analysis or care.

In one embodiment, an aggregator provides systems and methods available to physicians and their administrative staff (herein collectively referred to as physicians or doctors) to:
 book appointments on behalf of their patients online through a doctor directory and calendar function;
 filter available doctors by specialty, subspecialty, procedure, insurance participation and/or hospital network;
 transfer a patient's personal information, medical history and pre-selected insurance forms from one doctor's office to another's, electronically;
 transfer and upload relevant forms and paperwork via fax from one doctor's office to another;
 track referrals historically (over time) on a by-doctor or by-patient basis;
 facilitate referrals to and from doctors in a certain network or group.

These new features bring significant benefits to doctors and hospitals, increasing the efficiency of their workflows and improving patient care while reducing administrative costs, patient "leakage" (referrals outside the referring physician's network of providers), and the probability of errors in patient care.

In further embodiments, there are provided systems and methods for eliminating inefficiencies in the sharing of patient information, enabling, for example, the referring doctor to track a patient's progress after treatment by a specialist, thereby eliminating uncertainty and allowing more effective treatment in their next meeting.

In a further embodiment, systems and methods are provided for reducing patient non-compliance (e.g., failure to book or attend a scheduled appointment) with the physician referral process by establishing communication channels with the patient and the referred-to physician.

In a further embodiment, systems and methods are provided for reviewing a patient's progress after a referral appointment, by facilitating communications about the patient between the referring physician and the referred-to physician.

In a further embodiment, systems and method are provided for reviewing and reporting the results of one or more appointment referrals, enabling the referring physician to analyze the patient experience and/or quality of patient care, physician communication and history of (e.g., willingness and ability to accept) referral appointments by the referred-to physician.

In a further embodiment, systems and methods are provided for facilitating referrals to in-network or otherwise affiliated physicians.

In a further embodiment, systems and methods are provided for ensuring patient care after a hospital discharge.

In a further embodiment, systems and methods are provided for managing hospital emergency room capacity, including referring select patients to available primary care providers with available appointments to reduce the unnecessary use/expense of emergency room facilities.

In a further embodiment, systems and methods are provided for ensuring proper post emergency room care, enabling emergency room discharge staff to make appointments with qualified physicians to provide post-discharge care.

These and other embodiments of the invention are further described in the following detailed description and accompanying drawings.

According to one embodiment of the invention, an online physician referral apparatus is provided comprising:
 a computer apparatus for managing and storing a central managed database of physician profiles and scheduling information for physicians belonging to different provider groups, the database containing both physician profile data (PPD) and available appointment times for the physicians, wherein the PPD includes the physician's specialty, location and insurance or payment information; and
 an online portal, accessible by computer to referring physicians over a network, for computer implemented filtering of the PPD and available appointment times on behalf of a patient of the referring physician, the portal including a user interface enabling the referring physician to select and book on-line a referral appointment on behalf of the patient with one of the physicians based on a filtered combination of the available appointment times and PPD.

In one embodiment,
 the portal comprises a Web site and the user interface is accessible via a Web browser for filtering and selecting the one physician for the referral appointment.

In one embodiment,
 the PPD further includes one or more of an affiliation of the physician with a provider group, insurance carrier, insurance plan, and procedures performed.

In one embodiment,
 the database further includes the selected booked appointments and patient records relevant to such appointments.

In one embodiment,
 the database includes an identifier for correlating patient and patient records.

According to another embodiment of the invention, a method for online booking of physician referrals is provided comprising:
 a referring physician accessing an online portal to a central managed database of physician profile data (PPD) and available appointment times for physicians belonging to different provider groups, the PPD including the physician's specialty, location and insurance or payment information;

the referring physician performing the following steps via the portal:
 filtering the PPD and available appointment times on behalf of a patient of the referring physician and selecting, on behalf of the patient, a referral appointment with one of the physicians based on a filtered combination of the available appointment times and PPD;
 entering identification information for the patient; and
 booking the selected appointment for the identified patient.

In one embodiment, the PPD further includes one or more of an affiliation of the physician with a provider group, insurance carrier, insurance plan, and procedures performed.

In one embodiment, the filtering step is based on specialty and location and the portal displays a filtered listing of the physicians and their available appointment times.

In one embodiment, in response to the filtering, the portal displays a filtered listing of the physicians including their respective name, specialty, location, and insurance or payment information.

In one embodiment, the referring physician further performs the step of tracking one or more selected appointments.

In one embodiment, the tracking is performed based on one or more of the selected physician and the patient.

In one embodiment, the method further comprises the step of the referring physician transferring patient information to the selected physician.

In one embodiment, the method further comprises the step of the selected physician transferring patient information via the portal to the referring physician.

In one embodiment, the method further comprises the step of the referring physician reviewing on the portal a booking history of selected appointments.

In one embodiment, the booking history can be filtered by the referring physician based upon one or more of the patient, selected physician, specialty and date.

In one embodiment, the booking history comprises one or more of:
 appointment status;
 clinical information;
 patient identification information;
 selected physician;
 appointment time;
 appointment history; and
 further actions regarding the patient.

In one embodiment, the method further comprises the step of the referring physician establishing communication via the portal with one or more of the patient and the selected physician.

In one embodiment, the communications include one or more of a reminder to the patient and providing patient information to the selected physician.

In one embodiment, the method further comprises the step of the referring physician reviewing a history of the communications on the portal.

In one embodiment the method further comprises the steps of the portal displaying a description of the booked appointment and the referring physician printing the displayed description and providing the printed description to the patient.

In one embodiment, the portal is a website.

In one embodiment, the patient information can be uploaded by the referring physician to the portal.

In one embodiment, the patient information can be uploaded by the selected physician to the portal.

In one embodiment, a computer readable storage medium is provided with instructions to one or a plurality of computers for execution of the described methods.

According to another embodiment of the invention, a method for online booking of physician referrals is provided comprising:

a referring physician accessing an online portal to a central managed database of physician profile data (PPD) and available appointment times for physicians belonging to different provider groups, the PPD including the physician's specialty, location and insurance or payment information;

the referring physician performing the following steps via the portal:

filtering the PPD on behalf of a patient of the referring physician to select, on behalf of the patient, one of the physicians based on the PPD;

entering identification information for the patient; and notifying the selected physician electronically to arrange for a referral appointment.

In one embodiment, following the notification, the referring physician transfers patient information to the selected physician via the portal.

In one embodiment, the method further comprises the step of the referring physician tracking one or more of the appointment and the patient's progress via the portal.

According to another embodiment of the invention, a system for managing patient referrals is provided comprising:

an online portal, accessible by computer to a referring physician over a network, providing access to a central managed database of physician profile data (PPD) and available appointment times for physicians belonging to different provider groups;

the portal including a user interface enabling the referring physician to filter the PPD and available appointment times and select, on behalf of a patient of the referring physician one of the physicians for a referral appointment;

the portal providing one or more communication channels for communication between the referring physician and one or more of the patient and the selected physician for:

initiating and tracking toward completion the referral appointment of the patient with the selected physician; and transferring of patient information.

According to another embodiment of the invention, a network based scheduling system is provided, the system comprising:

an aggregator managed database containing information relevant to referring physicians who periodically need to schedule referral appointments with other physicians;

a set of parameters associated with each of a plurality of physicians accepting referral appointments having available appointment times;

a central controller managing a referral appointment schedule for the aggregator, wherein the central controller operates via a network to:

receive scheduling information via the network from the physicians accepting referral appointments;

supply available appointment times via the network to the referring physicians, with the supplied available appointment times determined by input received from the referring physician on behalf of a patient of the referring physician;

wherein the controller supplies an available appointment calendar via the network to the referring physician of the available appointment times, and wherein the referring physician can schedule an appointment via the network by selecting a desired appointment time.

In one embodiment, the network is the Internet.

In one embodiment, the aggregator provides a Web portal accessible to the physicians for receiving and supplying the scheduling and appointment times.

In one embodiment, the controller synchronizes the available appointment times with the appointment calendars of the physicians accepting referral appointments.

In one embodiment, the controller supplies a real time master schedule via the network.

In one embodiment, the controller operates via the network to supply tracking information relevant to the selected appointment.

In one embodiment, the tracking information includes one or more of:

patient contact information;

patient insurance information;

affiliation of the physician accepting referral appointments;

patient information supplied by the physician accepting referral appointments;

patient information supplied by the referral physician;

patient clinical information;

appointment history information;

physician notes concerning the patient

In one embodiment, the selecting is based on at least one of the specialty and procedures performed.

In one embodiment, the selecting is based on the specialty, location and insurance or payment information.

In one embodiment, the selecting is based on the affiliation.

In one embodiment, the selecting is based on the insurance or payment information and at least one of the specialty and procedures performed.

In one embodiment, the referring physician selects one of the displayed available appointment times.

In one embodiment, the filtering step is based on specialty, location, and type of insurance or payment information and the portal displays a filtered listing of the physicians and their available appointment times.

In one embodiment, filtering step is based on at least one of specialty, location, affiliation, procedures performed, and insurance or payment information and the portal displays a filtered listing of the physicians and their available appointment times.

In one embodiment, the referring physician enters insurance or payment information for the patient and the filtering step includes filtering based upon a match of the physician's insurance or payment information and the patient's insurance or payment information.

In one embodiment, the insurance information comprises one or more of an insurance carrier and an insurance plan.

In one embodiment, the referring physician enters a reason for an appointment, and the filtering step includes filtering based upon the entered reason.

In one embodiment, the patient identification information comprises one or more of the patient's email address, phone number, and name.

In one embodiment, the referring physician enters patient identification information for a new patient not existing in the database.

In one embodiment, the referring physician enters patient identification information for an existing patient in the database.

In one embodiment, the method further comprises the step of registering the referring physician to allow access to the portal.

In one embodiment, access to the portal is limited to referring physicians previously registered with the portal.

In one embodiment, the PPD includes an affiliation of the physician with a provider group and the tracking is performed based on the affiliation of the physician.

In one embodiment, the patient information includes one or more of clinical information, contact information, physician notes and insurance forms.

In one embodiment, the booking history includes links to additional information concerning one or more of the appointment, the selected physician and the patient.

In one embodiment, the links include one or more of insurance forms, patient clinical information, medical history, physician notes and appointment history.

In one embodiment, the communication comprises sending an electronic communication to the patient regarding the booked appointment.

In one embodiment, the central managed database is synchronized with one or more appointment calendars of the different provider groups.

In one embodiment, the booked appointment is synchronized automatically with a scheduling calendar of the selected physician.

In one embodiment, the physicians are not required to be registered with the portal.

In one embodiment, the central managed database further includes patient information comprising one or more of patient clinical information, patient contact information, patient insurance form, patient test result, and appointment history.

In one embodiment, the referring physician is notified of a missed appointment.

BRIEF DESCRIPTION OF THE FIGURES

FIG. 3 is one example of a webpage from an aggregator's website enabling a referring physician to identify potential specialists for a referral appointment according to one embodiment of the invention;

FIG. 4 is one example of an aggregator's webpage for entering patient insurance or payment information;

FIG. 5 is one example of an aggregator's webpage for entering patient information;

Figure 7:
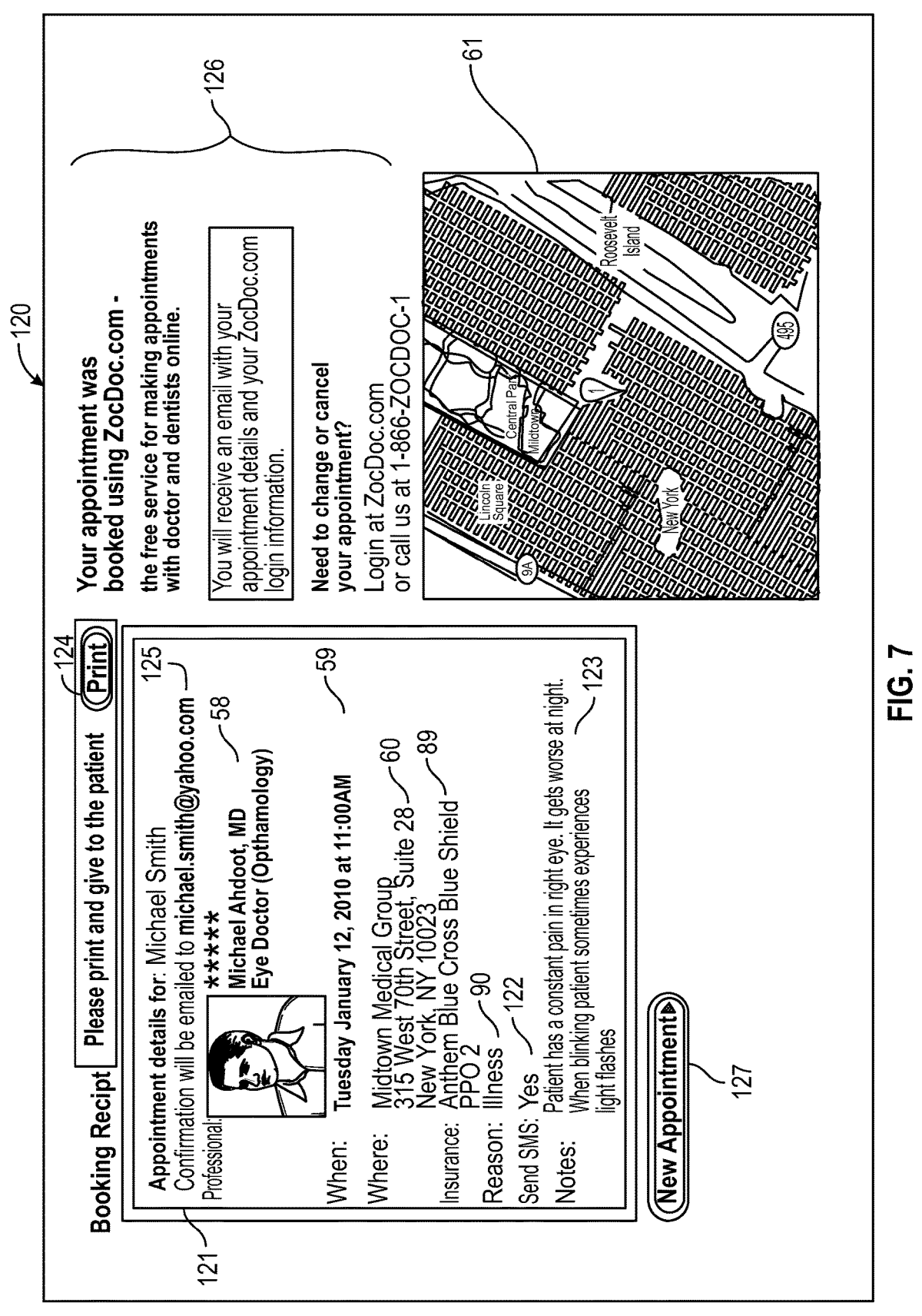

FIG. 7 is one example of an aggregator's webpage for printing confirmation of the referral booking;

FIG. 8 is one example of an aggregator's webpage allowing a referring physician to review a booking history of referral appointments;

FIG. 9 is one example of a more detailed webpage link to a specific patient in the booking history of FIG. 8;

FIG. 10 is another example of a linked webpage from the booking history of FIG. 8;

FIG. 15 is a schematic illustration of a method and apparatus according to another embodiment of the invention in which an emergency room administrator books a referral appointment;

FIG. 16 is a schematic illustration of a method and apparatus according to another embodiment of the invention in which patient records are transferred via the aggregator;

FIG. 18 shows one example of database records according to one embodiment of an apparatus and method of the invention containing stored referral appointment information.

DETAILED DESCRIPTION

Network Communications

Figure 1:
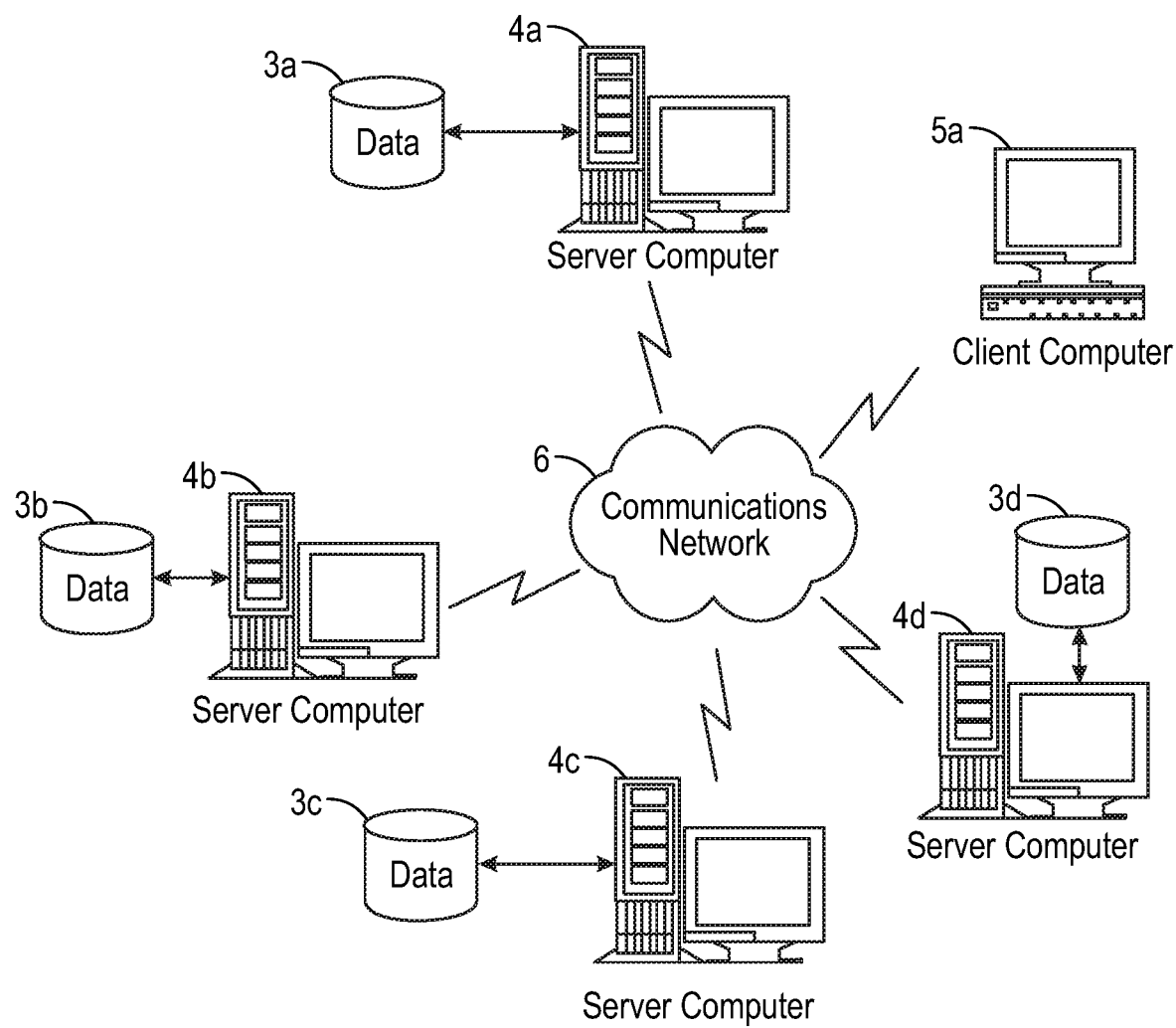
FIG. 1 is a schematic representation of an exemplary communications network for implementing various embodiments of the present invention.

Apparatus and methods are described herein for improving the patient referral process which enables online booking of healthcare appointments on a centralized service provider's (aggregator's) website. For these purposes, network based communications are required between one or more of the aggregator, physician practice groups, patients, hospitals and insurers. The block diagrams of one such communication system is illustrated in FIG. 1 and is meant to be representative only. Suitable hardware, communication protocols and software languages for implementing the systems and methods of various embodiments of the invention are readily known to those who are skilled in the art and any discussion herein is not meant to limit the scope of the invention.

FIG. 1 illustrates schematically network communications among various server computers 4a, 4b, 4c, and 4d and client computers 5a shown coupled together via a network or cloud 6 (e.g., the Internet) to communicate with one another using standard communication protocols, such as TCP/IP. The servers can be any type of server, including but not limited to a Windows, Unix, Linux and/or Apple servers. Each server may have an attached data storage system 3a, 3b, 3c and 3d for storing software applications and data.

In accordance with one embodiment of the invention, the network of FIG. 1 allows communications between a centralized service provider (aggregator), multiple healthcare practitioner practice groups, multiple hospitals, multiple insurers, and multiple patients. The aggregator's server provides a network based service to the practitioner groups, hospitals, insurers, and patients, e.g. an aggregator's server 4a provides a web-based data processing service and interface to each of the physician or patient computers 5a, practice group servers 4b, hospital servers 4c, and insurance provider servers 4d, and can also communicate electronically via email with each of these computers and servers. The aggregator's server also communicates (e.g. web-based) with each of the practice groups, hospitals and insurers via their respective servers for retrieving data such as available appointment times and other information for each of the practice groups, hospitals and insurers in order to enable online booking and confirmation of appointments on multiple websites. In alternative embodiments, the aggregator's service is provided to one or more practice groups, one or more hospitals, and/or one or more insurance provider(s). For ease of description, a first embodiment will refer to practice groups, it being understood that the services can similarly be provided to other healthcare provider groups.

Figure 2:
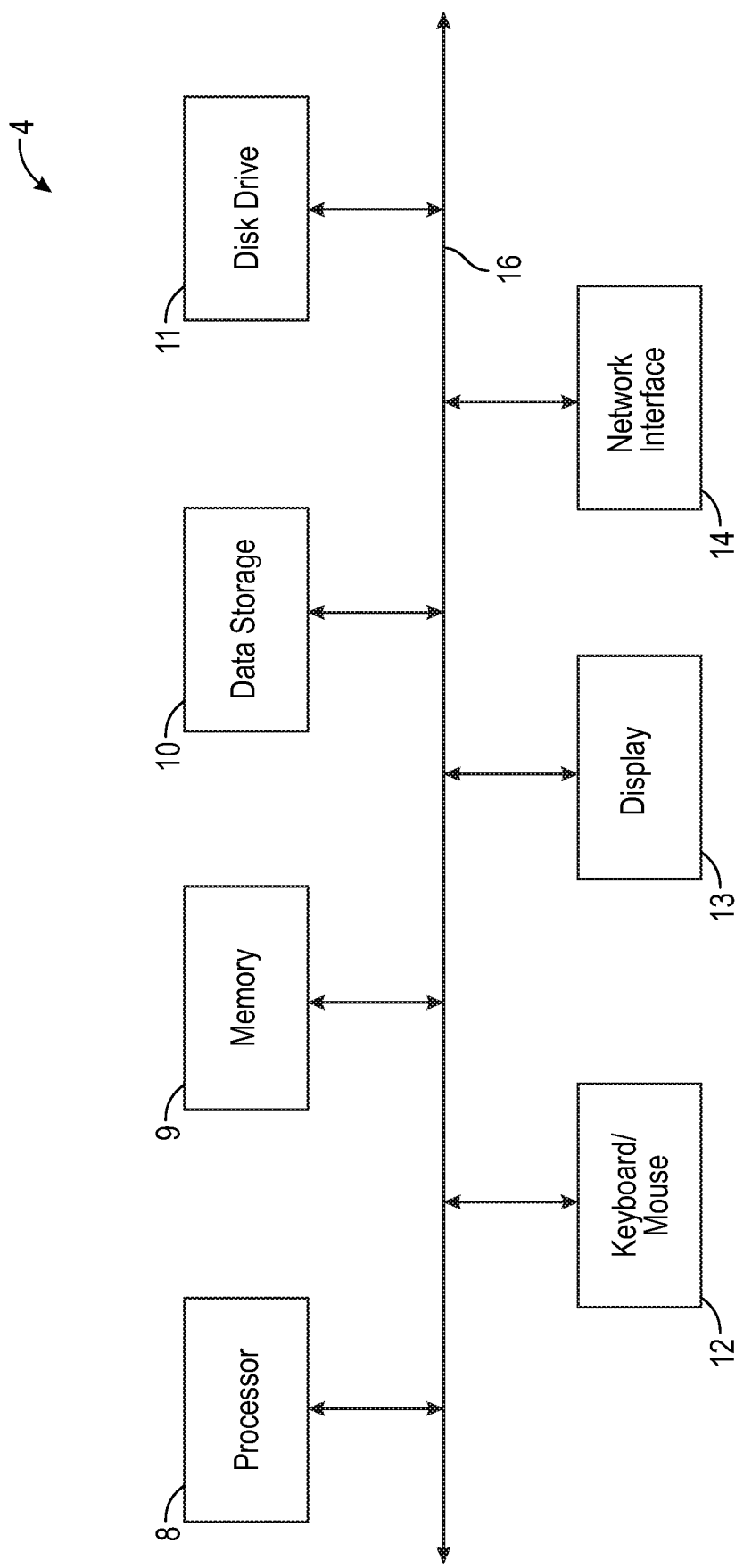
FIG. 2 is a block diagram of an exemplary computer on which the software product(s) of the present invention may be executed.

FIG. 2 is a block diagram of one server 4 which includes a processor 8, memory 9, data storage 10, disk drive 11, keyboard/mouse 12, computer display 13 and network interface 14. The components are coupled together and communicate via a system bus 16. Various software modules of the present invention can be loaded into data storage and during operation are transferred into memory (e.g. RAM) for execution by the processor. A user may manipulate the software and enter commands to the server using the keyboard/mouse. The input/output may be viewed on the display screen. The network interface couples the server to the Internet or whatever type of network is used to connect the server with the other computers and servers of the respective practice groups, patients, hospitals, insurers and aggregator. Further, the server may communicate with a storage array or storage network (e.g. SAN) if there is a need to access large amounts of data. A database of patient records, practice group (practitioner) records, and associated scheduling records may be implemented as a relational database and search engine with, for example, Microsoft's Active Server Page Technology, SQL Server Technology, Database Artisan Software, or database products from Oracle Corp., Redwood Shores, California.

The software described herein may be implemented as various modules, e.g. a web module, a database module, an email module, a facsimile module, and standard application programming interfaces (APIs). The web module may include a set of templates and icons to enable the creation of web pages. It may include other tools to allow one to create browser friendly websites. These tools enable the creation of dynamic hypertext web pages to be accessed by the practice groups, hospitals, insurers, patients and aggregator.

The database module may include a relational database and search engine. The records, fields, search queries and other features of the database are described below and suitable alternatives will be apparent to persons who are skilled in the art.

As used herein, database is meant to include any of various types of data repositories and processes for indexing, searching, storage and retrieval from such repositories.

The email module allows emails to be sent to/from patients, practice groups, hospitals, insurers and the aggregator via the respective server/computer. The emails can be sent manually by a person operating the server and can be automatically generated by the server. For example, the email module can be configured to automatically query the database module and send email messages to entities identified in the database module.

The software may include standard APIs so data and other information can be exchanged with other software systems.

Each practice group server may include the group's own practice management software and any other database of information used by the practitioners in that group. As described below, the aggregator may install software on the practice group's server for uploading available appointment times to the aggregator's database and otherwise automating and synchronizing the appointment calendars of the practice group and the aggregator. The relevant appointment booking information may be stored on one or both of the aggregator and practice group servers and data storage systems. Similarly, the aggregator may install software on a hospital's server and/or insurer's server for the same or similar purposes (e.g., exchange of profile information and/or appointment scheduling information).

The database maintained by the aggregator may include records of practitioner profile information and booking information for the practice groups and their respective practitioners, the hospitals and their affiliated practitioners, the insurance providers and their participating practitioners, and each patient who establishes an account with the aggregator. These records will be described further below in various embodiments.

Various systems and methods for aggregating available appointment times for multiple practitioner groups, including search and display algorithms are described in the following co-pending and commonly owned US patent applications:

U.S. Ser. No. 12/210,664 filed 15 Sep. 2008 entitled: CENTRALIZED MARKETPLACE FOR HEALTHCARE APPOINTMENTS ACROSS PRACTICE GROUPS;

U.S. Ser. No. 12/210,690 filed 15 Sep. 2008 entitled: CONSUMER PORTAL FOR HEALTHCARE APPOINTMENTS ACROSS PRACTICE GROUPS;

U.S. Ser. No. 12/210,765 filed 15 Sep. 2008 entitled: DATA SYNCHRONIZATION FOR BOOKING OF HEALTHCARE APPOINTMENTS ACROSS PRACTICE GROUPS; and U.S. Ser. No. 12/210,716 filed 15 Sep. 2008 entitled: PATIENT VERIFICATION FOR BOOKING OF HEALTHCARE APPOINTMENTS ACROSS PRACTICE GROUPS.

U.S. Ser. No. 12/722,728 filed 12 Mar. 2010 entitled: METHOD AND APPARATUS FOR MANAGING PHYSICIAN PROFILE AND HEALTHCARE APPOINTMENT SERVICES.

Physicians and Practice Groups

In various embodiments of the invention disclosed herein, the term "physician" or "doctor" refers to a physician administering patient care, as well as to those members of his staff responsible for maintaining the physician's calendar and/or patient records. Though the term is used interchangeably, it should be understood that in the exemplary figures and accompanying text, each function is being performed by one or more persons that perform such activities in a particular doctor's office on behalf of a physician.

The term "specialist" is applied to a physician administering secondary care to a patient after a referral from a referring physician, and is also applied to other members of his staff in the same manner as is done for a physician. It may be possible for any given physician to in one situation be a specialist (receiving a patient via referral), and in another be a primary care physician (referring a patient to another physician for specialized care).

Accordingly, in cases where primary care physicians and specialists work in integrated facilities and/or share administrative staff, the same staff member may process both the referral and its receipt. However, even if this were the case, there would still be authentication required on both ends of the referral process, meaning that there would still be effectively two users (one representing the referring physician, one the receiving specialist) involved, even if there was only one actual person responsible.

Further a "provider group" or "practice group" may be any entity linking a group of doctors through shared facilities, services, or referral agreements. This can include but should not be limited to integrated multi-facility hospitals, insurance networks, medical groups, and multi-doctor practices.

Online Booking of Referral Appointments

According to one embodiment of the invention, a portal referred to herein as a Referral Cockpit enables a referring (e.g., primary care) provider's office to initiate a search for and then select among a customized list of doctors based on a desired patient procedure, specialty, accepted insurances, affiliation with provider systems, and/or a number of further criteria (geographic location, gender, etc.). The office can then choose from available time slots in real time, and book a referral appointment online. This makes it far easier to ensure that the patient can see a specialist in close proximity and timely fashion. It also eliminates the possibility that the patient may forego necessary care due to the inconvenience of obtaining an appointment.

Each practice has the ability to edit their physician's displayed availability, accepted procedures, and accepted insurance plans. These data are stored on an aggregator database and made available to other medical professionals with access to the system. For many common practice management systems, availability can also be synchronized automatically with the doctor's existing calendar.

If a practice chooses not to display its availability in real time (or is not technologically capable of having someone maintain its calendar), or a patient does not yet want to decide on a time, the referring practice can still make a tentative appointment. A notification is then sent electronically to both the patient and the receiving (referred-to) practice. The patient's data now becomes accessible to the receiving practice, offering the opportunity to send reminders and arrange for the appointment at a later time.

Via the "Find Doctor" function (described below), a doctor or practice manager can input a patient's desired procedure, location, insurance provider and plan. These parameters serve to filter the view of the database provided to the referring party, and thus create a view of available appointments.

An example of an apparatus and method for online booking of referral appointments will now be described with respect to FIGS. 3-10.

Figure 3:
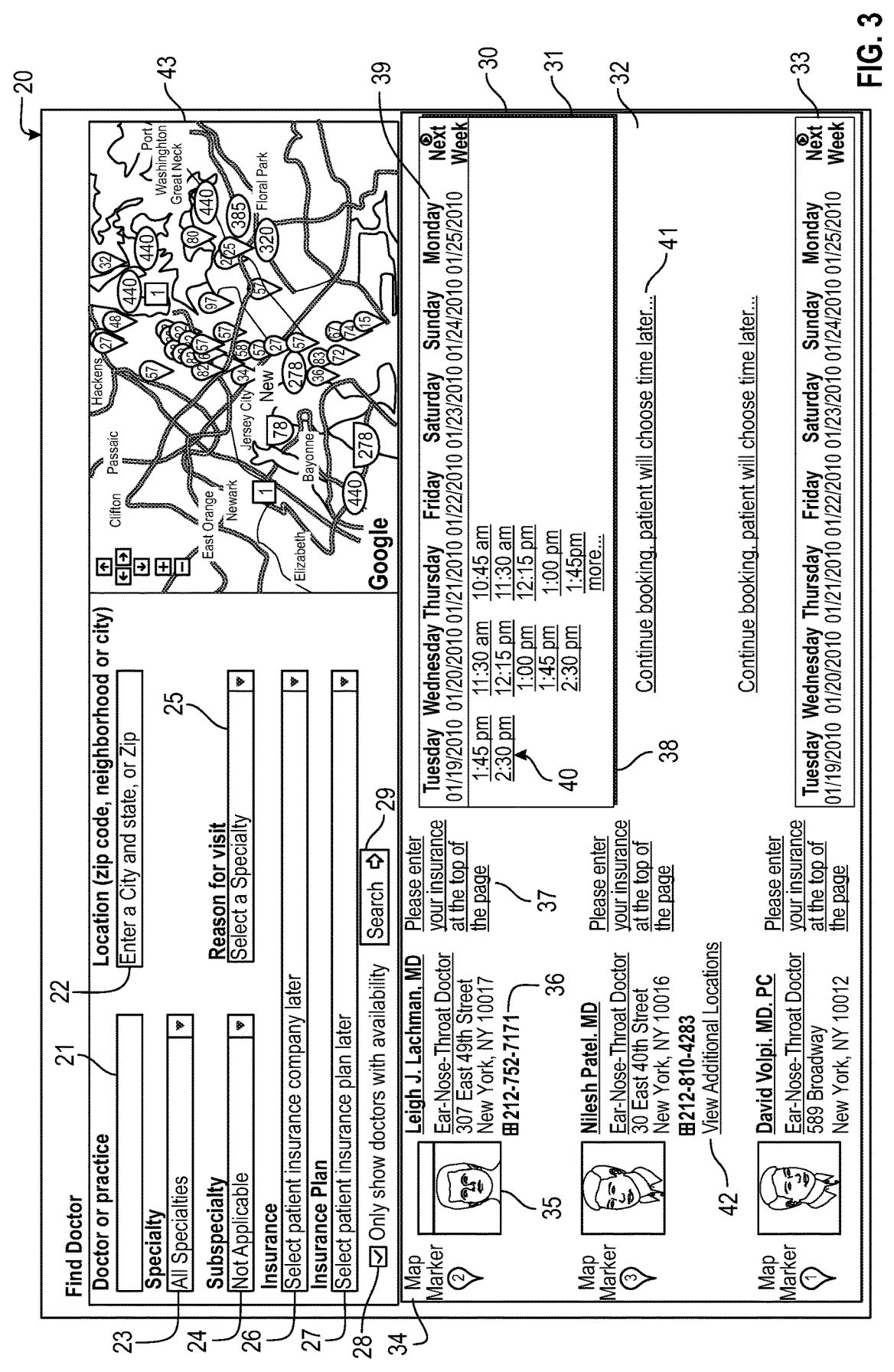

FIG. 3 is an example of a webpage 20 from an aggregator's website which enables a referring physician to filter profile data stored in the aggregator's central managed database for selecting an acceptable physician for the referral appointment.

The webpage entitled "Find Doctor" includes eight filtering (input) windows 21-28 prompting the referring physician to enter or select from a pull down menu, for the following items: doctor or practice 21, location (zip code, neighborhood, or city) 22, specialty 23, sub-specialty 24, reason for visit 25, insurance company 26, insurance plan 27, and a checkbox to select "only show doctor's with availability" 28. The referring physician enters the appropriate information and then clicks the search button 29, initiating the search of the aggregator's database based on the entered filtering information. Not all items (fields) are required for the search, rather the referring physician can pick among the windows based upon his or her knowledge of the specific patient, medical condition, desire to select a physician within an affiliated network, and/or location. As one example, the referring physician enters the specialty 23 and location 22. Below the filtering windows 21-28 is a results window 30, containing a list of potential receiving physicians that satisfy the filtering criteria. In this example, there is a separate row of information for each receiving physician; FIG. 3 shows the initial three rows 31, 32, 33 for the first three physicians. Each row includes a first column containing a numbered map marker 34 which also appears in another window 43 located on the upper right hand corner of the page, the window 43 being a geographical display (street map) showing the location of the physician's office by the same numbered marker. If the physician has additional practice locations, this is indicated by a link 42 (as shown for the physician in the second row), wherein clicking on the link 42 will identify and display additional map marker numbers, with corresponding markers on the geographical display 43. Next to each map number 34, proceeding in serial order across the page, there is provided (where available) a photo of the physician 35 and name and contact information for the physician 36; the information 36 may include a link for accessing additional profile information concerning the physician. In the next row there is a link 37 which prompts the user to enter the patient insurance information at the top of the page (windows 26, 27), if not already provided. Next is a grid display 38 of available appointment times for this physician. The grid includes column headings across the top with designations 39 for various days of the week, and an advance button to select subsequent weeks. Below each day of the week, there are individual links 40 for each available appointment time. This enables the referring physician to simply click on an appointment time link 40, to select an appointment on behalf of the patient. Alternatively, if a physician does not wish to select an appointment time now, there is an alternative process (link 41) enabling the patient to select an appointment time at a later date, as discussed further below.

Figure 4:
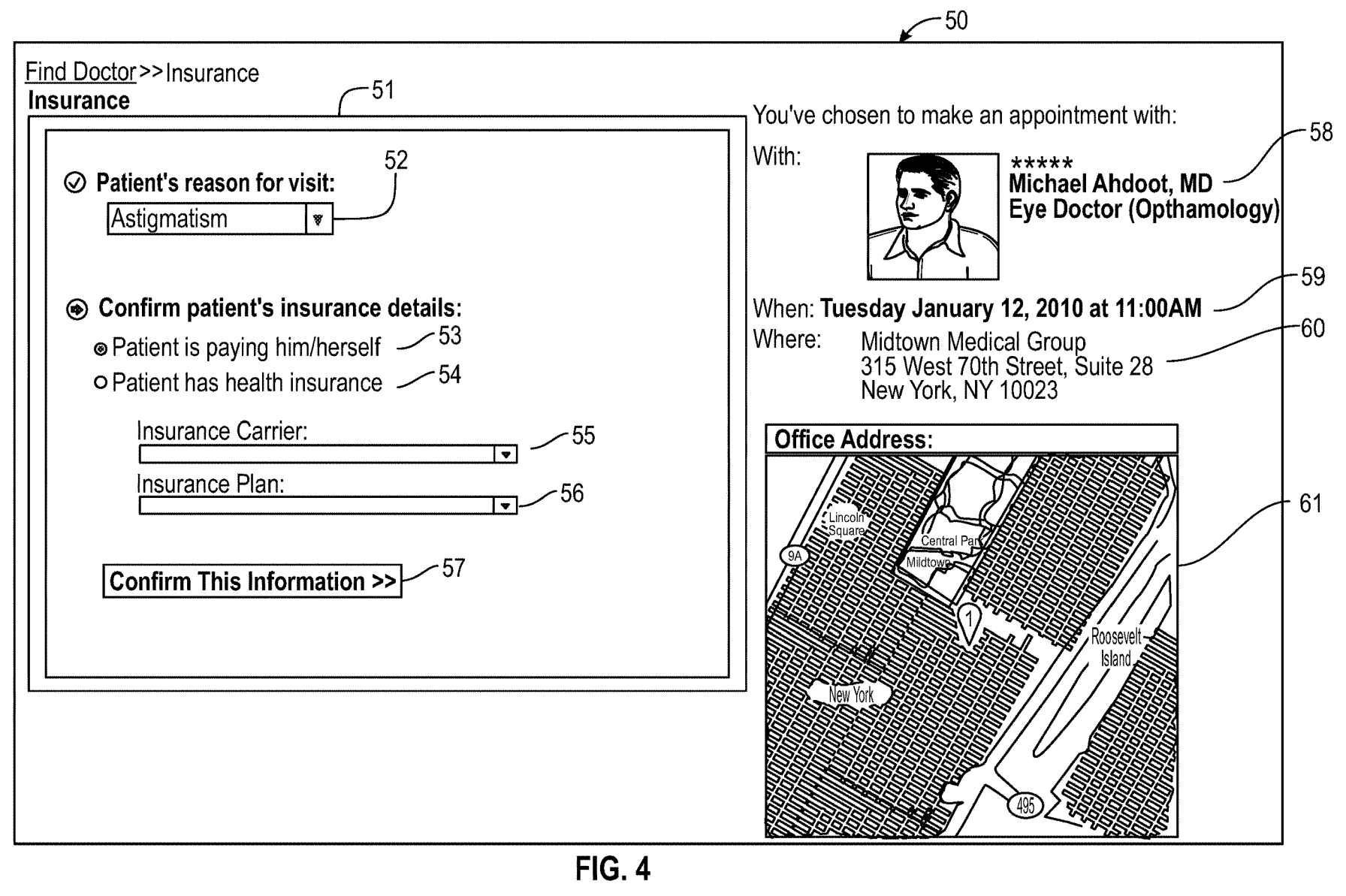

Assuming the referring physician has selected an appointment time on the web page of FIG. 3, the selected appointment time for the selected physician is then processed by the aggregator's software and the aggregator's website displays web page 50 shown in FIG. 4. In the left hand box labeled insurance 51, the referring physician is now prompted to enter in the first filter window 52 a reason for the patient's visit, which may be selected from a pull down menu, and to confirm the patient's insurance details, namely whether the patient is paying himself 53, whether the patient has health insurance 54, entering the name of the insurance carrier 55, and entering the name of the insurance plan 56. The referring physician then hits the button 57 to confirm the entered information. On the right hand side of this page 50, the display includes the referred-to physician identification information 58, the time and date of the selected appointment 59, the location of the appointment 60 and a geographical display 61 with a map marker showing the location of the appointment.

Figure 5:
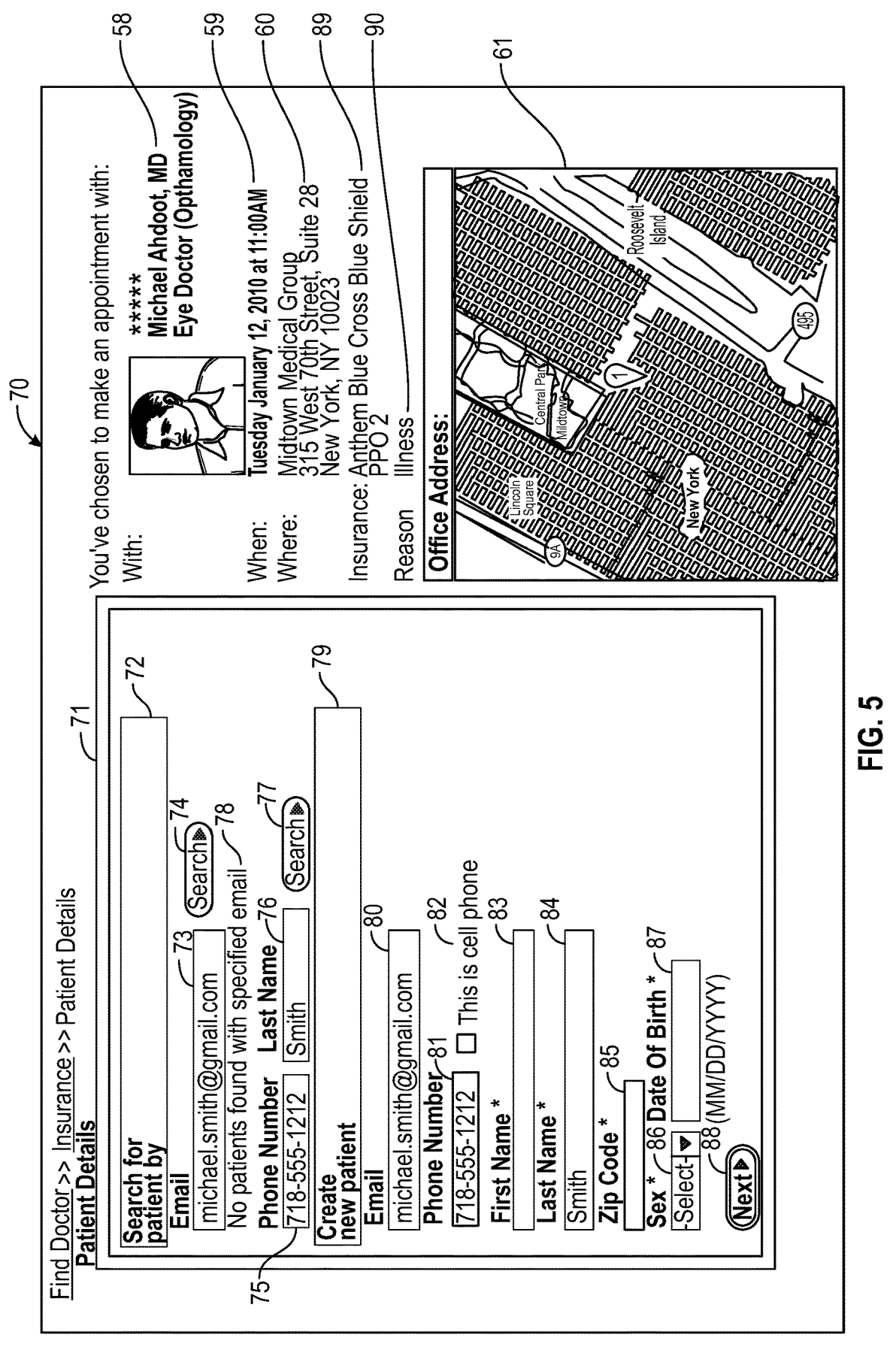

Once the referring physician clicks the confirmation button 57 in FIG. 4, the entered information is processed by the aggregator's software and the aggregator's website returns a web page 70 shown in FIG. 5. This page, entitled Patient Details, includes on the left hand side a window 71 for entry of patient identification information. There are two options, either the referring physician enters identifying information for the patient in the upper portion 72, to determine if the patient is previously included in the aggregator database, or else the referring physician creates a record for a new patient not previously existing in the database, in the lower portion 79. Assuming the patient already exists in the database, in this example he can be located either by entering his email address in window 73 and clicking the search button 74, or alternatively entering his phone number in window 75 and his last name in window 76 and clicking the search button 77. If no patient is found with the specified email, the referring physician will be so notified at 78.

If the referring physician needs to create a new patient record, the referring physician then enters the following information in the designated boxes, the required information being designated with an asterisk: email address in window 80, phone number in window 81, whether the phone number is a cell phone in window 82, patient first name 83, patient last name 84, patient zip code 85, patient gender 86, and patient date of birth 87.

The referring physician then clicks the next button 88 and the aggregator's software processes the entered information. Meanwhile, on the right hand side of the page 70, there is again shown, similar to the right hand portion of FIG. 4, the same physician identification 58, time and date of the appointment 59, location of the appointment 60, and geographical display 61. In addition, there is shown in FIG. 5 the patient insurance information 89 and reason for the visit 90.

Figure 6:
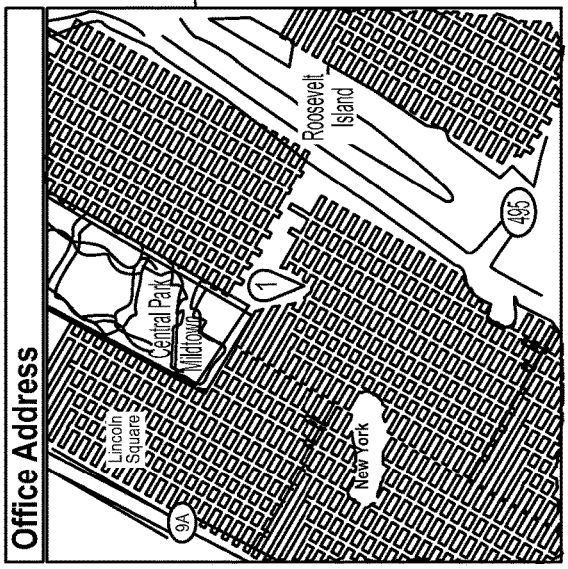
FIG. 6 is one example of an aggregator's webpage for confirming the booking of a referral appointment.

Once the referring physician clicks one of buttons 74, 77 or 88 on web page 70, the process accepts the entered information and returns a next web page 100 shown in FIG. 6. This page, entitled "Confirm Booking", includes on the left hand side a window 101 which confirms the identity of the patient 102 and prompts the referring physician to establish a communication channel with one or more of the patient 103 and referred-to physician 106. Window 101 includes the patient's email address, to which an email confirmation of the appointment will be sent 104. If the referring physician wishes to also send a text reminder to the patient, he so indicates this in input box 105. The referring physician can also establish a communication channel 106 with the selected (referred-to) physician. The referring physician may enter notes concerning the patient and/or appointment in the entry window 107. The referring physician may click a link 108 to send a pre-completed referral form specific to the patient and his insurance company, to the referred-to physician. The referring physician may also elect to have files sent to the referred-to physician, as indicated in window 109. Each of the selected files 110 is listed in a box, and a removal button 111 is provided in the event the referring physician elects to not send the file. Entry window 112 enables a physician to locate an additional file and attached that file 113 to the transmission. Finally, the referring physician clicks the book it button 114, whereby the selected communications will be sent to the patient and referred-to physician respectively. Web page 100 also displays the same physician/appointment information 58-61 and 89-90 as the prior web page 70.

After electing to book the appointment by clicking button 114 on web page 100, the process books the appointment and returns a web page 120 with a booking receipt. The booking receipt includes on the left-hand side a window 121 confirming the details of the appointment, including the same information 58-60 and 89-90 provided in the prior web pages. In addition, the booking receipt indicates whether a text reminder will be sent to the patient at 122, and includes any notes 123 entered by the referring physician. The receipt indicates that a confirmation email has been sent to the patient's email address at 125. The referring physician now has the option to print the booking receipt and give a copy to the patient, by clicking the print button 124. The booking receipt further provides the patient with contact information for the aggregator, enabling the patient to contact the aggregator if the patient wishes to change or cancel the appointment. The referring physician may now proceed to schedule a new appointment, by clicking the new appointment button 127.

Transfer of Patient Records

Over the course of a multi-doctor treatment process, a patient's medical records must often be transferred between several offices. Each of these transfers carries with it the possibility of document loss, and the frequent use of physical (paper) patient records only serves to increase this risk. Patients themselves often do not know which records and forms they will need, meaning that despite their interest in ensuring an efficient transfer, they are ill-equipped to do so.

There is no widely used standardized procedure in place to efficiently facilitate transfer of records between offices, meaning that a responsible patient and cooperative, well-organized practices must be present to ensure each doctor is properly informed. Three-way communication between the patient and both practices is at best cumbersome, and at worst ineffective in ensuring that records are transferred completely and in timely fashion. Regional Health Information Organizations (RHIOs) do attempt to solve this problem by integrating into clinical systems, defining common ontologies and standardizing quantitative results. However, these systems are typically limited to institutional settings, don't filter information for what is necessary for the referral, and thus tend to suffer from very limited adoption. They tend to be used mostly in emergency settings where no referral was made. Breakdowns in communication and record transfers can lead to unnecessary procedures, inappropriate medication, and superfluous testing that combine to create additional costs for patients and insurance providers, all the while eroding trust in medical providers and causing frustration on all sides.

According to further embodiments of the invention described below, a method and apparatus are provided which allows different practice groups to easily make patient information available to one another. Furthermore, a referring doctor can track a patient's progress after treatment by a specialist, eliminating uncertainty and allowing for more effective treatment at their next meeting. Document loss becomes a non-issue, as digitally archived documents on the aggregator's servers cannot be lost or misplaced.

Personal patient contact and insurance plan data are stored on the aggregator's central database, and made available to pass on to a referred-to doctor. Patients' records are matched on the basis of their email address or phone number registered with the aggregator. This information can be transmitted automatically in conjunction with the appointment request.

Insurance forms are saved in digital form in the aggregator's database, and can be pre-filled with this data and sent in digital form to the receiving practice in conjunction with the appointment request. Records can be uploaded by scanning them, or by faxing them under a system-generated cover page to the aggregator (where in turn they are digitized automatically and stored in the aggregator's database). For example, a system-generated cover page may feature a bar code, which allows the aggregator's computers to identify the faxed record and its intended recipient, and forward it on automatically to that location by email. Records can also be outputted as faxes at practices where this is necessary or preferred. These processes require no additional equipment other than that present today in almost all medical offices, i.e., fax machine at minimum.

Tracking the Referral Process

Further embodiments of the invention will now be described which enable a referring physician to track his historical and ongoing referral appointments. This tracking and management process solves several recognized problems with current methods and can enhance patient care. After a discussion of the problems this new system and method addresses and overcomes, a specific embodiment will be described with respect to FIGS. 8-10.

Reducing Patient Non-Compliance

Patient non-compliance is a major inefficiency factor in the physician referral process. No patient can be relied upon completely to book and attend a referred appointment. Referred appointments not kept may endanger the patient's health, are lost revenue for the receiving doctor, and may increase overall healthcare costs if the patient's condition becomes worse because he did not receive timely care.

Non-compliance can also cause legal problems, as a referring physician may have a legal obligation to make a referral when it is deemed to be necessary. Adverse health effects following non-compliance in a system without standardized documentation procedures exposes physicians to potential legal challenges—a patient or a patient's relatives may become convinced that no proper referral was given, and place the onus on the physician to prove otherwise.

The Referral Cockpit described below increases the likelihood of patient compliance. An appointment made at the time of referral, in the referring doctor's office, and communicated to the patient in writing and by e-mail is far more likely to lead to a successful referral appointment than current procedures, which in some cases are as basic as simply providing a patient with a list of qualified specialists and contact information. Furthermore, making a specific appointment through the Referral Cockpit involves the receiving practice in the patient's care. This practice now has the ability to contact a patient with reminders (see above), further reducing non-compliance. The Referral Cockpit's documentation functions ensure that compliance with legal referral obligations is recorded and unquestionable.

The status of referral appointments past and scheduled can be tracked by the referring practice using an "Appointment Status" indicator as described below. A "Suggested Action" indicator provides the doctor or his staff with one-click access to a patient's contact information, further simplifying the process of following up on referrals. A referring practice is thus also informed immediately and automatically of a missed referral appointment.

Post-Referral Reporting on Patients

At present, there is no convenient procedure doctors use to follow up on a patient's progress after a referral appointment. Primary care providers are obligated by law to follow up on patients they have referred, but frequently are frustrated by the need to proactively contact other practices. In many cases, several attempts at contact must be made to administer a single patient, a process that creates inefficiencies and extra costs while increasing the likelihood of errors. Patient proactivity would offer no solution in consideration of the fact that a layman patient, in most cases lacks a sufficient understanding to pass medical findings along effectively. This imperfect and haphazard state of affairs has negative implications in terms of the quality of care provided. It also hinders primary care providers from scheduling follow-up appointments, which are important from a medical standpoint and also generate revenue.

The present invention provides doctors with a tool for managing communications on a patient-by-patient basis via the Referral Cockpit. They can see their colleagues' (referred-to physicians) findings and prepare themselves accordingly prior to their follow-up appointment with a patient. Doctors can communicate about patients through patient-specific channels, thus ensuring that these exchanges are not forgotten amidst other work.

Documents can be easily made available using the aggregator's database either by scanning or using the fax process described earlier. The Referral Cockpit's search interface allows for communications to be filtered on a patient-by-patient basis, allowing each doctor to see the entire history of documentation and data exchanged and offering a tangible improvement over prior means of communication.

A "Booking History" search function (described below) provides a doctor an overview of referrals given. Referrals can be filtered by physician, specialty, and/or appointment date. "Appointment Status" and "Suggested Action" functions can again be used to provide a quick overview of steps to be taken for a specific patient, eliminating the prior need to analyze each patient's file and follow up where necessary.

Post-Referral Reporting on Doctors

By referring patients to another physician, a doctor effectively grants a colleague access to trust-based doctor-patient relationships that form the core of his or her business. It is accordingly in the referring doctor's interest, both from a professional standpoint and with a view to his or her own reputation, to ensure that patients referred elsewhere receive care quickly and efficiently, and that they are satisfied with their patient experience. Without a tool to systematically track post-referral care, doctors rely on intuition when deciding where to refer their patients. Other than time consuming individual follow-ups to every referral, there is little a doctor can do to gain an overview of and assess the doctor-patient relationships being built between "his" or "her" own patients and the specialists he or she refers to.

Comprehensive reporting on referrals is a central feature of the Referral Cockpit. This allows doctors to more objectively evaluate professional relationships, which in turn should create benefits for patients hoping to be referred to reliable and competent doctors. Practices deficient in sharing documents, accepting referred patients at the time desired, or making use of information shared can be more easily identified.

Post-referral reporting on doctors is available via the "Booking History" function using the same search interface as for post-referral reporting on patients. The post-referral tracking can be sorted based on referred-to physician.

Booking History

The embodiment illustrated in FIGS. 8-10 will now be described. FIG. 8 shows a web page 130 on the aggregator's website that enables the referring physician to track referral appointments. The page, entitled "Booking History", includes a number of filtering windows in an upper portion 131, enabling the referring physician to filter based on selected criteria and generate a booking history report. Here, the filtering windows include two windows 132-133 for entering a date range, a window 134 for selecting a particular patient (or leaving the window 134 blank to select all patients), a window 135 for selecting a specific referred-to physician (or leaving the window 135 blank to select all referred-to physicians), a window 136 for filtering based on specialty of the referred-to physician, and a window 137 for identifying a criteria for sorting the results, e.g., by patient name or referred-to physician. By clicking the generate report button 138, the aggregator's process filters the entered information and generates a report, such as the booking history 140 shown in the lower portion of web page 130. Here, the booking history report includes a grid of rows and columns, arranged in reverse appointment date order, for a plurality of referral appointments. Across the top of window 140 there are a plurality of fields (column headings) 141 which include, in serial order across the page: appointment status 142, results 143, patient name and phone number 144, referred-to physician 145, appointment date 146, appointment history 147, and suggested actions 148. Ten row entries 150-159 are illustrated below, each row being specific to a particular referral appointment. For example, the first row entry 150 indicates that patient Michael Smith (field 144) was referred to physician Alexander Arkansas (field 145) for an appointment on May 24, 2010 (field 146), and that the appointment was booked on May 2, 2010 (field 147). In the first column (field 142), Michael Smith's appointment status is awaiting confirmation. In other row entries, alternative appointment status indicators include confirmed (row 152), rescheduled (row 153), patient cancelled (row 154), received results (rows 155 and 158), awaiting results (row 156), practice cancelled (row 157) and patient no-show (row 159). In the results column 143, an icon is displayed if results of the appointment have been stored on the aggregator's database. In the last column 148, there is a link identifying a suggested action to be taken, e.g., contact patient if the patient has either cancelled or did not show up for the referral appointment. This prompts the referring physician to communicate with the patient for establishing a new appointment.

If this example (FIG. 8), the row entry 155 for patient Richard Smith is highlighted and selected by the referring physician on web page 130; this action causes a more detailed referral history for the appointment to be displayed, as shown in FIG. 9. In FIG. 9, the web page 170 now includes an enlarged window 171 with a referral summary for patient Richard Smith. The referral summary includes, in serial order starting at the top of the window 171, identification of the referred-to physician, his specialty, the reasons for the patient visit and the date and time of the appointment 172. By clicking on the button 173, the received results of the appointment can be displayed. Below box 172, there is provided a link 174 for displaying the insurance referral form. Below this, there is a box 175 for displaying the attachments, namely the files shared by the referring and referred-to physicians (three files are shown). For each file 176 three options (link or checkbox) are provided enabling the referring physician to download the file 177, remove the file 178, or refax the file to the referred-to physician 179. In addition, the referring physician can click a link 180 to add another attachment and click button 181 to refax the selected attachments to the referred-to physician. Below this, there is a results display 182 which here includes a link 183 for reviewing the EKG results of the appointment. Below this, there is an entry box 184 enabling a physician to enter a message to the patient, and a button 185 for sending the message to the patient. Below this, there is provided (partially shown) a similar message window 186 for entering a message to the referred-to doctor, and a button (not shown) for sending the message to the referred-to doctor.

FIG. 10 shows a complete referral summary in window 191 on the web page 190. This alternative provides a more detailed report for the selected patient Richard Smith and includes the same text 172 and button 173 as in FIG. 9. The referral summary provides an audit trail 194 which lists in serial order going down the window, a reverse chronological list of events concerning the referral appointment. Here, the illustrated events include an entry 195 that results were added to the aggregator's database by the referred-to physician 195, a message sent to the referred-to doctor 196, a message sent to the patient with a link to show the message 197, patient confirmation 198, and various attachments that were faxed 199, 201-203 or added 200, 204 to the database.

The above embodiments illustrate select features of the invention for both online booking and tracking of referral appointments. These same features are useful in a variety of healthcare provider practices, as described further below.

Facilitating Referrals to In-Network and Affiliated Physicians

Large hospitals and hospital networks often employ or maintain affiliations with primary care providers. Ideally, these primary care providers should refer patients for secondary or tertiary care within the hospital network they are affiliated with. This would ensure continuity of care and records, benefitting the patient, while benefitting the hospital. Without in-network referrals, the cost of care at integrated facilities increases. Similarly, investments that could benefit patients become more difficult to undertake.

By offering instant access to each specialist's calendar through the Referral Cockpit, a hospital or hospital group can provide its physicians with a real incentive to refer within network—speed and ease of use. Referrals within network can be made significantly more quickly, increasing the speed of care. Furthermore, search results within the Referral Cockpit can be narrowed down to just in-network doctors, offering physicians a quickly accessible view of professionals within their network. The Cockpit's integrated document-sharing features also serve to ensure continuity of care, reducing the hospital's exposure to malpractice allegations. Finally, by adopting the Cockpit a hospital (group) can ease for its administrators the task of monitoring a doctor's use of their in-network colleagues when referring. Overall, the likelihood of in-network referrals increases, creating benefits for the hospital while improving the quality of care for patients.

The benefits described above occur by leveraging the Referral Cockpit's individual functions, and applying them as an enterprise solution rather than an improvement to a single practice's infrastructure. Pre-selection of in-network doctors can occur by accessing saved affiliation data stored on the aggregator's database.

Ensuring Care after Hospital Discharges

A patient's need for medical care does not typically end once discharged from a hospital. Usually, a number of follow-up appointments are necessary. The hospital is obligated to instruct the patient to undertake these if there exists a medical necessity. However, at present, there exists no standardized framework for ensuring that these appointments actually occur, or that post-discharge care fulfills the objectives envisioned by a hospital's physicians and their discharge teams.

Using the Referral Cockpit, a hospital's administrative staff can instantly transfer records of and book appointments for a patient about to be discharged. This fulfills the hospital's legal obligations and decreases the likelihood of inadequate care after discharge. Furthermore, it does also provide integrated hospital facilities or hospitals operating within a large provider network the opportunity to keep the patient in-network, especially in cases where a patient may not have an existing relationship with the medical provider(s) he or she is recommended to continue seeing.

No additional functions of the Referral Cockpit, other than those already described, are necessary to implement this application.

Managing Emergency Care Facility Capacity

Many hospital emergency rooms are frequently over capacity. They treat a variety of patients, ranging from those without serious ailments to life-threatening cases. Furthermore, many patients enter the emergency room simply because they do not have immediate access to their preferred primary care provider, or because they do not have a primary care provider. While primary care capacity elsewhere goes unutilized, emergency rooms find themselves struggling to cope with a deluge of patients, increasing wait times for all as well as the risk of mistakes and inadequate care.

Emergency room staff working with the Referral Cockpit can identify low-priority cases, and access a real-time view of available primary care providers in the vicinity. This helps decrease waiting times, provides patients with faster access to care, and allows physicians and medical staff to concentrate their efforts on those patients in the greatest need of true emergency care. Furthermore, the Referral Cockpit can be used to steer patients to providers within the same provider network as the emergency facility.

The Referral Cockpit's core functions, as described above, are all equally applicable in this scenario. The Cockpit's documentation features serve to create a record of the emergency facility having fulfilled its obligation to provide care.

Ensuring Post-Emergency Care

In 2009, the Annals of Emergency Medicine published the results of a study showing that fully 78% of emergency care patients did not fully understand the instructions given to them[1]. Of all patients, 34% found themselves unclear about their post-emergency care. Furthermore, handwritten communication was found to be a major source of patient confusion. Patients unclear about what to do once they leave

[1] "Patient Comprehension of Emergency Department Care and Instructions: Are Patients Aware of When They Do=Not Understand?" *Annals of Emergency Medicine*, Vol. 53 Issue 4, April 2009. Study attached.

the emergency room are at risk of eschewing needed follow-up care, causing adverse effects on their health. Their situation can degenerate to the point where more emergency care is required. This state of affairs is inefficient, costly and dangerous, and exacerbated even further by the fact that even comprehending patients are often found to be non-compliant, as described above.

Emergency room staff can use the Referral Cockpit to make a confirmed appointment with a physician qualified to provide post-discharge care. Once this appointment is made, reminders can be sent to the patient in the time leading up to the appointment, and documents transferred electronically to the receiving physician. Each of these steps increases the possibility of patient compliance and efficient post-emergency care.

Emergency care facility staff can use the Referral Cockpit's booking function to make appointments. The documentation functions described above serve to ensure that the receiving physician is well-informed before administering follow-up care.

EXAMPLES

FIGS. 11-16 further illustrate various embodiments of the invention as described below.

Figure 11:
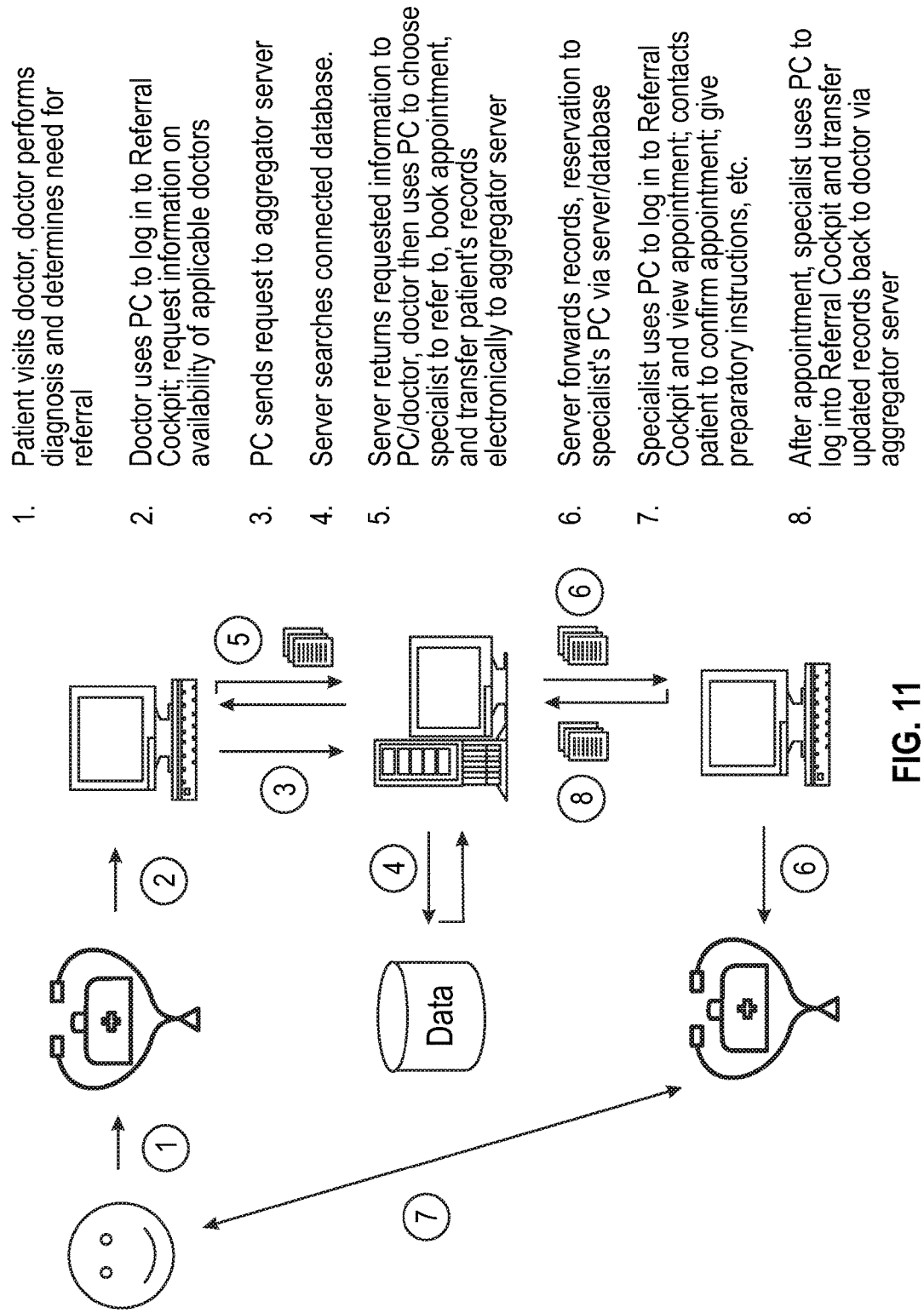
FIG. 11 is a schematic illustration of one method and apparatus for booking referral appointments in which both the referring physician and specialist utilize the Referral Cockpit.

FIG. 11 illustrates the following example:
Case 1—Referral Cockpit to Referral Cockpit
1. Patient visits doctor, doctor performs diagnosis and determines need for referral;
2. Doctor uses PC to log in to Referral Cockpit; request information on availability of applicable doctors;
3. PC sends request to aggregator server;
4. Server searches connected database;
5. Server returns requested information to PC/doctor, doctor then uses PC to choose specialist to refer to book appointment, and transfer patient's records electronically to aggregator server;
6. Server forwards records, reservation to specialist's PC via server/database;
7. Specialist uses PC to log in to Referral Cockpit and view appointment; contacts patient to confirm appointment, give preparatory instructions, etc.
8. After appointment, specialist uses PC to log into Referral Cockpit and transfer updated records back to doctor via aggregator server.

Figure 12:
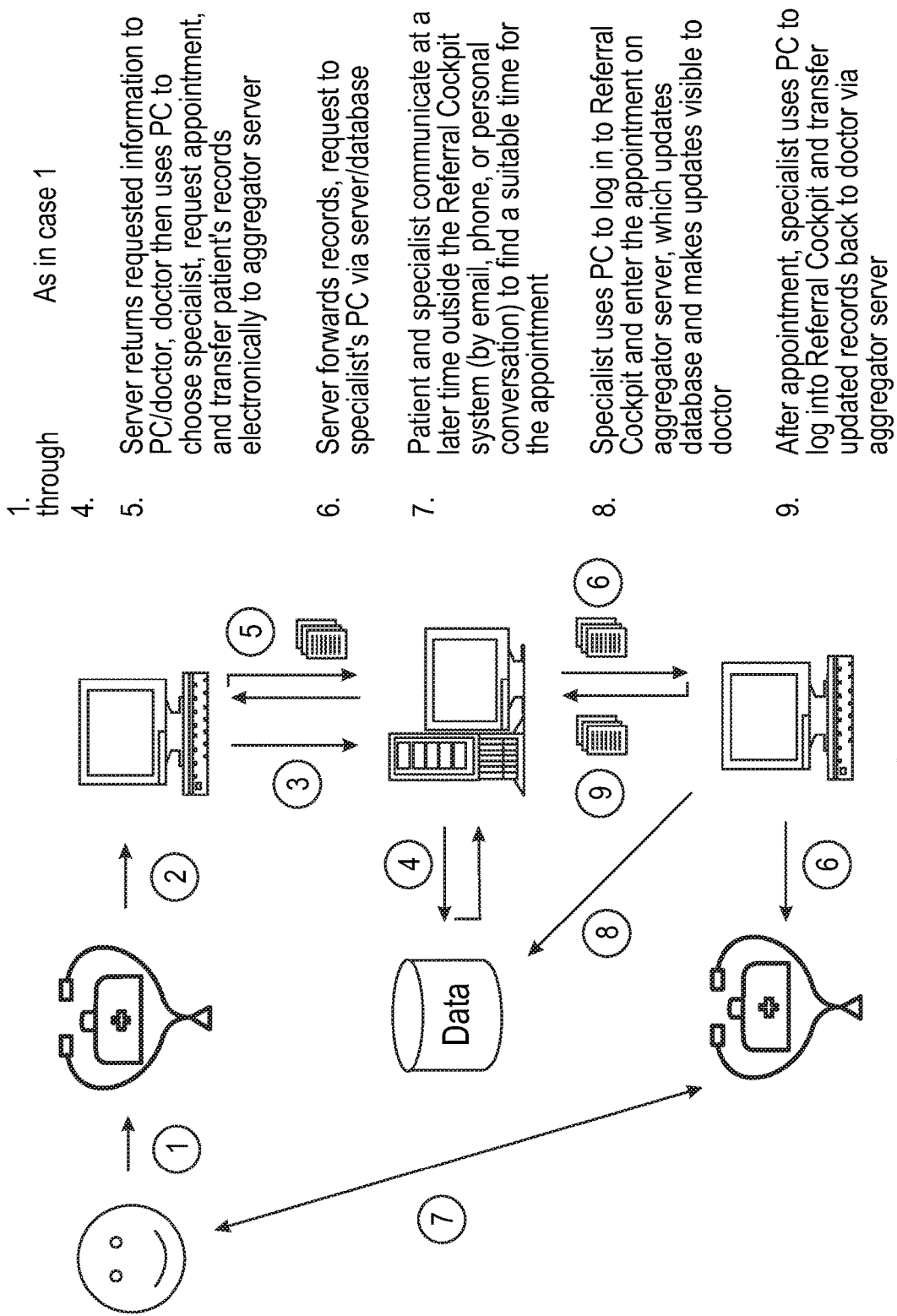
FIG. 12 is a schematic illustration of a method and apparatus according to one embodiment of the invention in which the referring physician postpones selection of a specific appointment time.

FIG. 12 illustrates the following example:
Case 2—Referral Cockpit to Referral Cockpit, No Time Chosen
1. Patient visits doctor, doctor performs diagnosis and determines need for referral;
2. Doctor uses PC to log in to Referral Cockpit; request information on availability of applicable doctors;
3. PC sends request to aggregator server;
4. Server searches connected database;
5. Server returns requested information to PC/doctor, doctor then uses PC to choose specialist, request appointment, and transfer patient's records electronically to aggregator server;
6. Server forwards records, request to specialist's PC via server/database;
7. Patient and specialist communicate at a later time outside the Referral Cockpit system (by email, phone, or personal conversation) to find a suitable time for the appointment;
8. Specialist uses PC to log in to Referral Cockpit and enter the appointment on aggregator server, which updates database and makes updates visible to doctor;
9. After appointment, specialist uses PC to log into Referral Cockpit and transfer updated records back to doctor via aggregator server.

Figure 13:
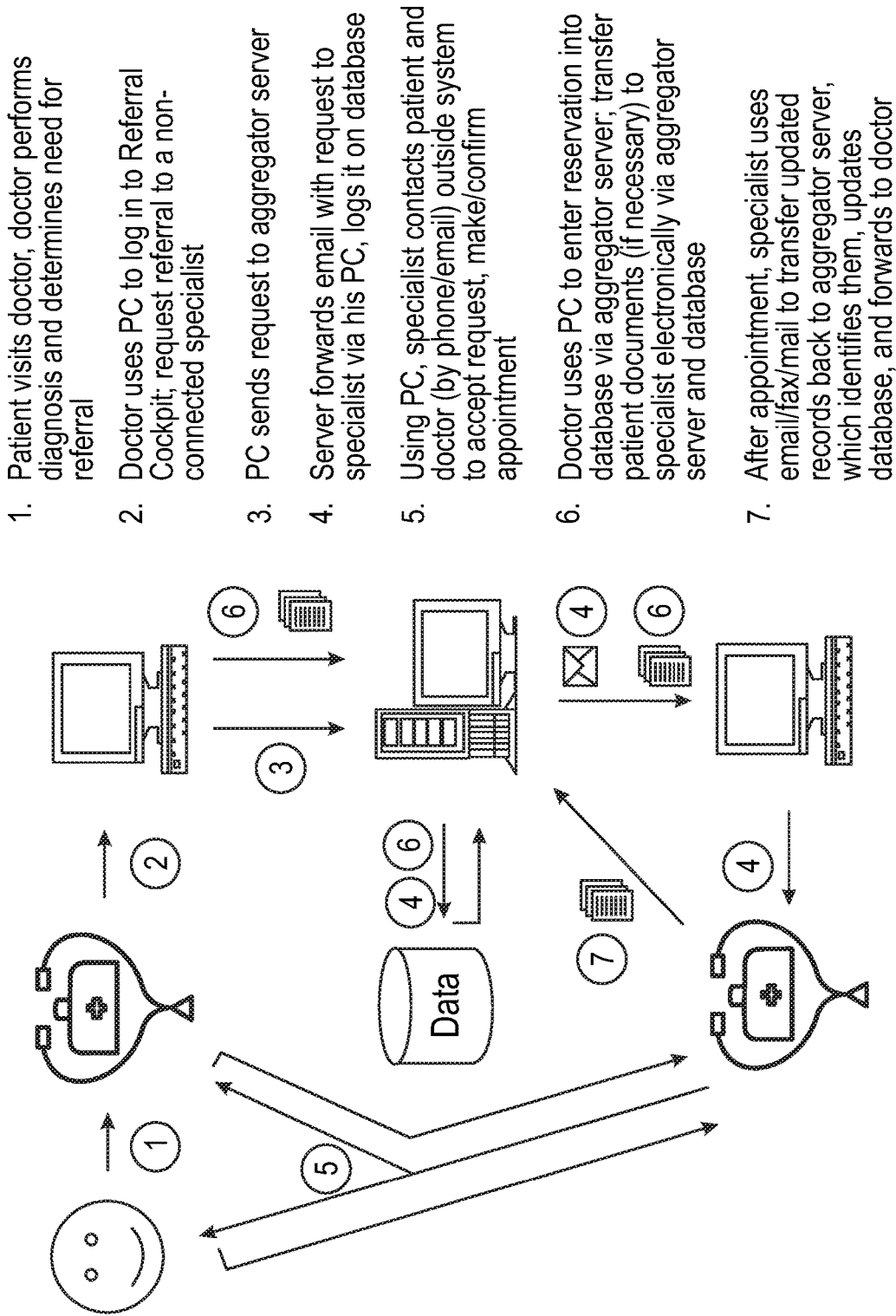
FIG. 13 is a schematic illustration of a method and apparatus according to one embodiment of the invention in which a referring physician books a referral appointment outside the Referral Cockpit system.

FIG. 13 illustrates the following example:
Case 3—Referral to Practice Outside Cockpit System that Uses PCs
1. Patient visits doctor, doctor performs diagnosis and determines need for referral;
2. Doctor uses PC to log in to Referral Cockpit; request referral to a non-connected specialist;
3. PC sends request to aggregator server;
4. Server forwards email with request to specialist via his PC, logs it on database;
5. Using PC, specialist contacts patient and doctor (by phone/email) outside system to accept request, make/confirm appointment;
6. Doctor uses PC to enter reservation into database via aggregator server; transfer patient documents (if necessary) to specialist electronically via aggregator server and database;
7. After appointment, specialist uses email/fax/mail to transfer updated records back to aggregator server, which identifies them, updates database, and forwards to doctor.

Figure 14:
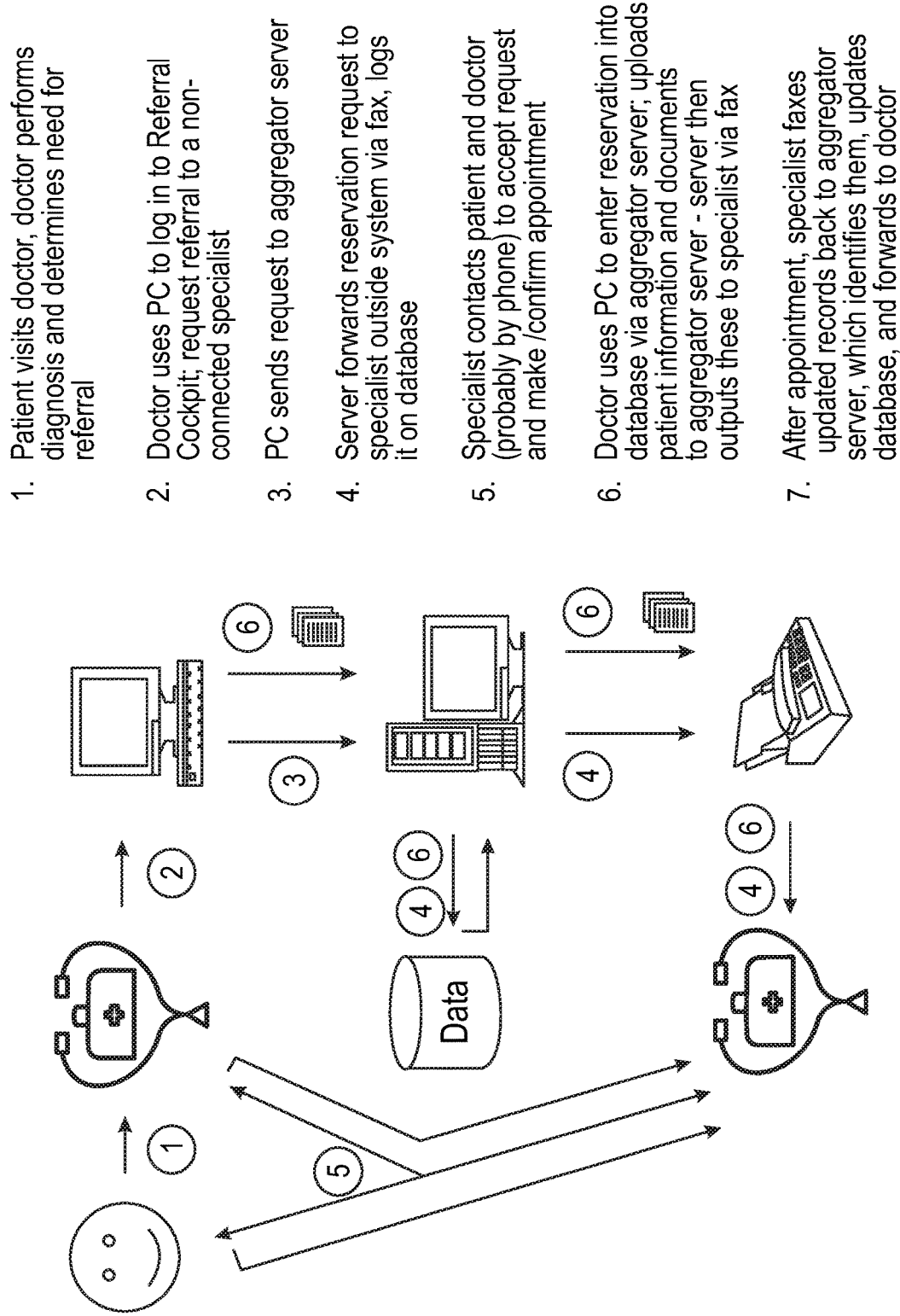
FIG. 14 is a schematic illustration of a method and apparatus according to another embodiment of the invention in which the referring physician books an appointment outside the Referral Cockpit system.

FIG. 14 illustrates the following example:
Case 4—Referral to practice outside Cockpit system not using PCs
1. Patient visits doctor, doctor performs diagnosis and determines need for referral;
2. Doctor uses PC to log in to Referral Cockpit; request referral to a non-connected specialist;

3. PC sends request to aggregator server;
4. Server forwards reservation request to specialist outside system via fax, logs it on database;
5. Specialist contacts patient and doctor (probably by phone) to accept request and make/confirm appointment;
6. Doctor uses PC to enter reservation into database via aggregator server; uploads patient information and documents to aggregator server—sever then outputs these to specialist via fax;
7. After appointment, specialist faxes updated records back to aggregator server, which identifies them, updates database, and forwards to doctor.

FIG. 15 illustrates the following example:

Case 5—Referral within a Hospital System
1. Patient visits emergency room, doctor diagnoses need for referral to specialist;
2. Emergency room administrator uses PC to log in to Referral Cockpit, request information on availability to doctors;
3. PC sends request to aggregator server;
4. Server searches connected database;
5. Server returns requested information to ER admin. Admin chooses in-network specialist to refer to, book appointment, and transfer patient's records electronically to aggregator server;
6. Server forwards records, reservation to specialist's PC via server/database;
7. Specialist uses PC to log in to Referral Cockpit and view appointment; contacts patient to confirm appointment, give preparatory instructions, etc. —patient later visits specialist;
8. After appointment, specialist uses PC to log into Referral Cockpit and transfer updated records back to ER admin via aggregator server.

FIG. 16 illustrates the following example:

Case 6—Paper Record Transfer Via Aggregator Server/Database
1. Doctor scans paper records, which scanner transfers to PC;
2. Doctor uses PC to log in to Referral Cockpit, upload scanned records, which are then transmitted to aggregator server;
3. Aggregator server matches records with existing patient and case records, updates database, creates bar-coded cover page;
4. Records are now forwarded directly to specialist via fax or PC in fax or email form, and/or specialist can re-request automated delivery or records as necessary via fax or PC at will, and without again involving doctor. If specialist is outside system, records he/she emails or faxes back to aggregator server will automatically be identified using bar code, database will be updated, and doctor sent records via Cockpit.

Database Structures

Figure 17:
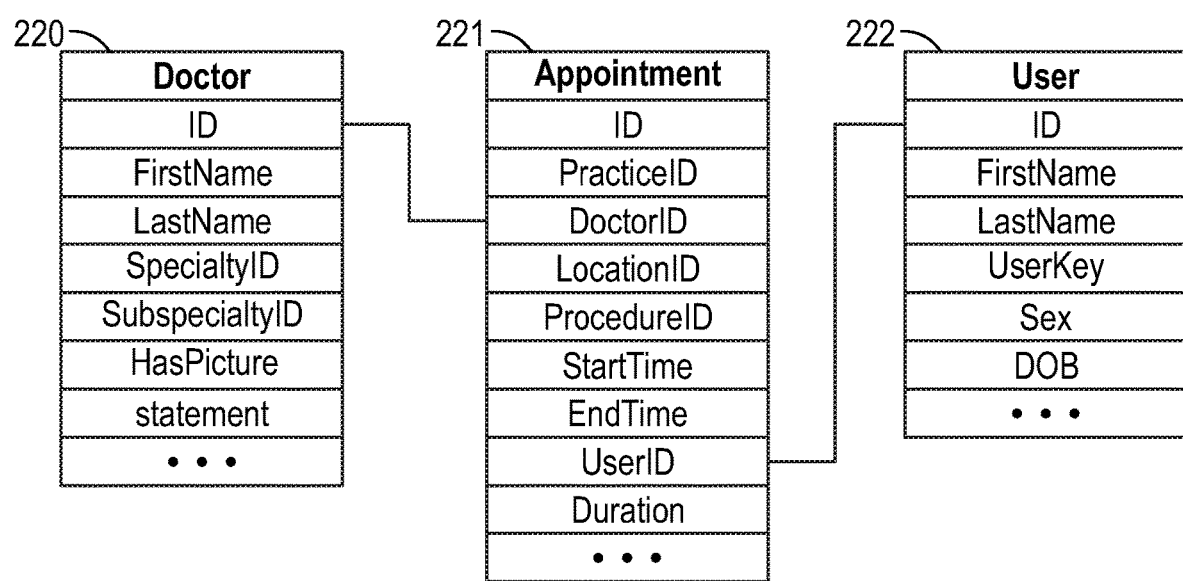
FIG. 17 is one example of a database structure according to one method and apparatus of the invention in which the aggregator database uses stored doctor and patient data to enable the booking of a referral appointment.

FIG. 17 illustrates one example of a database structure for use in one or more embodiments of the method and apparatus of the invention. An aggregator database uses various stored tables of doctor, appointment, and user data for implementing the booking of a referral appointment. As shown, the doctor information table 220 may include a unique physician identifier (ID), physician name, specialty and sub-specialty identifiers, photo and physician statement information. An appointment table 221 may include a unique appointment identifier, practice identifier, physician identifier, location identifier, procedure identifier, start and end time for the procedure, a user identifier and duration. A user table 222 may include a unique user identifier, name, user key, gender and date of birth. This use of a relational database is meant to be illustrative of just one possible embodiment and not limiting.

FIG. 18 illustrates one example of a stored appointment table for use in one or more method or apparatus embodiments of the invention. The stored records of appointments in the aggregator's database may include each of the following fields:
ID;
practice ID;
doctor ID;
location ID;
procedure ID;
start time;
end time;
user ID;
duration.

Again, this is one example of a table of stored referral appointment information utilizing the doctor, appointment and patient information stored in the aggregator database and is not meant to be limiting.

System, Method and Computer Program

As will be appreciated by one skilled in the art, the present invention may be embodied as an apparatus or method, including a computer system or computer program product. Accordingly, unless specified to the contrary, the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present invention may take the form of a computer program product embodied in any tangible medium of expression having computer-usable program code stored in the medium.

Any combination of one or more computer-usable or computer-readable medium(s) may be utilized, unless specified to the contrary herein. The computer-usable or computer-readable medium may be, for example but not limited to, electronic, magnetic, optical, electromagnetic, infrared, or semiconductor storage mediums. More specific examples (a non-exhaustive list) include: a portable computer diskette, a hard disk, a random access memory (RAM), a read-only memory (ROM), an erasable programmable read-only memory (EPROM or Flash memory), and a portable compact disc read-only memory (CDROM), an optical storage device.

Computer program code for carrying out operations of the present invention may be written in any combination of one or more programming languages, including an object oriented programming language such as Java, Smalltalk, C++, C#, JavaScript/Ajax and similar programming languages. JavaScript, which relies on a runtime environment in a web browser, is commonly used for website development (e.g., writing functions that are embedded in or included from HTML pages). JavaScript can be used as a scripting language for implementing an Ajax-embedded webpage. Unless otherwise specified, the program code may execute entirely on a user's computer, partly on the user's (e.g., server or client) computer, as a stand-alone software package, partly on a user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

A website is a collection of web pages posted on one or more web servers, accessible via the Internet. A webpage is a document, typically written in [X]HTML, that is generally accessible via HTTP, a protocol that transfers information from a web server to a display in the user's web browser. The collection of publically accessible websites are referred to as the "World Wide Web".

Websites are written in, or dynamically converted to, HTML (hyper text mark-up language) and are accessed using a software interface known as the user agent. Web pages can be viewed or otherwise accessed from a range of computer-based and Internet-enabled devices of various types, including desktop computers, laptop computers, PDA's and cell phones. A website is posted on a computer system known as a web server, and it includes software that retrieves and delivers the pages in response to requests from the website users.

A dynamic website presents variable information that is tailored to particular users. It may accept the user's input and respond to a user's request. For example, the user can enter text into a data entry field or form or select highlighted (linked) options, which prompts the website to fulfill the request and return a unique result. The aggregator's website, accessible in various forms to patients, hospitals, insurers and practice groups, includes such dynamic functionality.

A link or hyperlink, is a reference or navigation component in a document to another section of the same document or to another document on a different domain. A web browser usually displays a link in some distinguishing way, e.g. in a different color, font or style. When the user activates the link (e.g. by clicking on it with the mouse) the browser will display the target of the link.

As used herein, database and central database are not meant to be limiting, and may reside in one or more locations and/or data repositories. The aggregator's database is referred to as a central database to distinguish it from the separate multiple databases of the unaffiliated practice groups from which the aggregator combines (aggregates) the available appointment times to be offered on the aggregator's website. Database as used herein is not meant to be limiting and may include various forms of data repositories and applications for indexing, search, storage and retrieval of such repositories.

The aggregator can, by collecting and storing this available appointment data from a plurality of unaffiliated practice groups, provide a much larger database of available appointment times/specialties/procedures and can allow patients to book appointments directly with the aggregator, without requiring the patients to contact the practice group in any manner (by phone, email or practice group website).

The present invention is described above with reference to flowchart illustrations and/or block diagrams of methods, apparatus and computer program products (systems) according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The flowchart and block diagrams illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

By way of example only, various described embodiments may be implemented on processor based servers, such as any x86_64 processor based server, for example running a Windows Operating System, e.g. Windows Server 2003, Windows XP/Vista, including Microsoft's NET Framework (e.g. Net 2.0). The database programming may be implemented in the SQL programming language (e.g. MS SQL 2005 and TSQL).

Modifications can be made to the previously described embodiments of the present invention and without departing from the scope of the invention, the embodiments being illustrative and not restrictive.

The invention claimed is:

1. A method comprising:
providing, on multiple practice group servers, a synchronizer application configured to automatically synchronize appointment availability data from the multiple practice group servers to an aggregator database;
providing, by an aggregator server and to a user computing device, an online interactive user interface having a plurality of dynamic input fields;
receiving, by the aggregator server and from the user computing device, an electronic request specifying an input into one or more of the dynamic input fields, the input comprising a specialty and a geographic location;
comparing, by the aggregator server, the electronic request with physician profile data and the appointment availability data in the aggregator database to generate a display of available appointment times for physicians associated with the specialty and within a predetermined distance to the geographic location;
displaying, by the aggregator server and on the interactive user interface, a listing of the physicians and their available appointment times based on the comparison;

receiving, by the aggregator server and from the user computing device, a selection of an available appointment time for a listed physician via the interactive user interface;

booking, by the aggregator server and to a selected practice group server chosen from the at least one of the practice group servers, the selected available appointment time for the listed physician as a referral appointment for a patient via the synchronizer application;

transferring, by the aggregator server and to the selected practice group server, the one or more digital records for the patient, wherein the one or more digital records are stored in the aggregator database;

receiving, by the aggregator server and from the selected practice group server, tracking information for each referral appointment, wherein the tracking information includes at least an appointment status and an appointment history for each referral appointment, and storing the tracking information in the aggregator database;

receiving, by the aggregator server and from the user computing device, an electronic tracking request for at least one referral appointment;

generating, by the aggregator server, a referral history in response to the tracking request, the referral history including at least the appointment status and the appointment history for the at least one referral appointment;

modifying, by the aggregator server, the interactive user interface to display the referral history;

receiving, by the aggregator server and from the at least one of the practice group servers, one or more updated digital records for the patient including medical treatment information; and displaying, by the aggregator server and on the interactive user interface, the patient medical treatment information.

2. The method of claim 1, wherein the tracking information includes accepted appointments, shared documents and communications with the selected practice group server.

3. The method of claim 1, wherein the tracking information is filtered based on one or more of:
 a date range;
 a patient;
 a referred-to physician; or
 a specialty or a procedure of the referred-to physician.

4. The method of claim 1, further comprising:
 generating, by the aggregator server, a comparison of multiple referral histories for display on the interactive user interface.

5. The method of claim 1, wherein the referral history further comprises suggested actions.

6. The method of claim 5, wherein the suggested actions include one or more of:
 generating a communication with a patient for booking a new appointment;
 displaying patient information supplied by the practice group server;
 displaying patient clinical information;
 displaying appointment history information;
 displaying physician notes concerning the patient;
 entering a message to the patient;
 entering a message to the practice group server; or
 downloading a file on the network from the practice group server.

7. The method of claim 1, further comprising:
 receiving, by the aggregator server and from the practice group server, shared documents, and storing the shared documents in the aggregator database.

8. The method of claim 7, wherein the physician profile data includes affiliations of a referred-to physician with one or more of the practice group servers, and wherein the applicable available appointment times are filtered based on the affiliations of the referred-to physician.

9. The method of claim 1, wherein the applicable available appointment times are filtered based on the specialty or a procedure.

10. The method of claim 9, wherein the interactive user interface displays a filtered listing of referred-to physicians including their respective specialties, procedures and affiliations.

11. The method of claim 1, wherein the physician profile data includes affiliations of a referred-to physician with one or more of the practice group servers, and wherein the tracking request is based on one of the affiliations of the referred-to physician.

12. The method of claim 1, wherein the physician profile data comprises affiliations of a referred-to physician with one or more of the practice group servers, and wherein the tracking request is based upon one or more of a patient, the referred-to physician, an affiliation, a specialty or a procedure.

13. The method of claim 1, wherein the referral history comprises one or more of:
 the appointment status;
 the appointment history;
 clinical information;
 patient identification information;
 a referred-to physician;
 an appointment time; or
 further actions regarding the patient.

14. The method of claim 1, further comprising:
 receiving, by the aggregator server and from the user computing device, a request to establish communication via the interactive user interface with the practice group server.

15. The method of claim 14, wherein the communications comprise one or more of a reminder to a patient or providing patient information to the practice group server.

16. The method of claim 14, further comprising:
 displaying, on the interactive user interface, a history of the communications.

17. The method of claim 1, wherein the interactive user interface comprises a website.

18. The method of claim 1, wherein the user computing device comprises an Internet enabled device.

19. The method of claim 1, further comprising:
 receiving, by the aggregator server and from the user computing device, patient clinical information uploaded via the interactive user interface.

20. The method of claim 1, further comprising:
 receiving, by the aggregator server and from the provider group server, patient clinical information.

21. The method of claim 1, further comprising:
 displaying, on the interactive user interface, a booking receipt comprising the selected available appointment time of the referral appointment.

22. The method of claim 1, wherein the synchronizer application is configured to automatically synchronize physician profile data and appointment availability data from multiple practice group servers prior to booking the referral appointment.

* * * * *